United States Patent
Mills et al.

(10) Patent No.: US 8,354,454 B2
(45) Date of Patent: Jan. 15, 2013

(54) PRODRUGS OF OXAZOLIDINONE CETP INHIBITORS

(75) Inventors: Sander G. Mills, Scotch Plains, NJ (US); Amjad Ali, Freehold, NJ (US); Cameron Smith, Lawrenceville, NJ (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 90 days.

(21) Appl. No.: 13/121,972

(22) PCT Filed: Sep. 21, 2009

(86) PCT No.: PCT/US2009/057657
§ 371 (c)(1),
(2), (4) Date: Mar. 31, 2011

(87) PCT Pub. No.: WO2010/039474
PCT Pub. Date: Apr. 8, 2010

(65) Prior Publication Data
US 2011/0218177 A1    Sep. 8, 2011

Related U.S. Application Data

(60) Provisional application No. 61/194,915, filed on Oct. 1, 2008.

(51) Int. Cl.
*A61K 31/135* (2006.01)
*C07C 211/03* (2006.01)
*C07C 211/54* (2006.01)

(52) U.S. Cl. ........ 514/650; 564/305; 564/336; 564/342; 514/579; 514/646

(58) Field of Classification Search .................. 564/305, 564/336, 342; 514/579, 646, 650
See application file for complete search history.

(56) References Cited

U.S. PATENT DOCUMENTS

| | | | |
|---|---|---|---|
| 7,652,049 B2* | 1/2010 | Ali et al. | 514/376 |
| 7,737,295 B2* | 6/2010 | Ali et al. | 560/115 |
| 7,910,592 B2* | 3/2011 | Ali et al. | 514/255.05 |
| 7,915,271 B2* | 3/2011 | Ali et al. | 514/274 |
| 2008/0119476 A1 | 5/2008 | Ali et al. | |

OTHER PUBLICATIONS

Gomes et al. Cyclization-Activated Prodrugs. Molecules, 2007, vol. 12, pp. 2484-2506, p. 2486, para 1 to p. 2488, para 1; Scheme 2; Scheme 3; Scheme 4.
Saari et al. Cyclization-Activated Prodrugs. Basic Carbamates of 4-Hydroxyanisole., J. Med. Chem. 1990, vol. 33, pp. 97-101, Scheme 1, Table 1; para 2; p. 99, para 8.
US Search Report for PCT/US09/57657; Performed, Nov. 6, 2009; by Authorized Officer—Lew W. Young.

* cited by examiner

*Primary Examiner* — Golam M M Shameem
(74) *Attorney, Agent, or Firm* — James L. McGinnis; Catherine D. Fitch

(57) ABSTRACT

The compounds of Formula I are pro-drugs of CETP inhibitors having a central oxazolidinone ring. The compounds cyclize by the elimination of HX to form an oxazolidinone ring after administration to a patient.

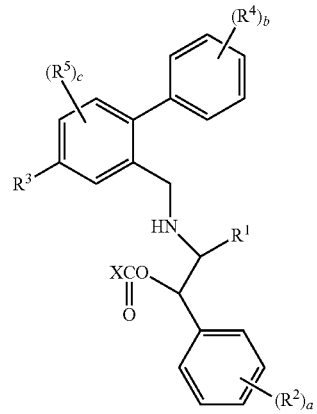

I

17 Claims, No Drawings

PRODRUGS OF OXAZOLIDINONE CETP INHIBITORS

CROSS REFERENCE TO RELATED APPLICATIONS

This application is a National Stage filing under 35 U.S.C.§371 of PCT/US2009/057657, which was filed Sep. 21, 2009, and which claims priority under 35 U.S.C.§119 (e) from U.S. Application No. 61/194,915, filed Oct. 1, 2008.

FIELD OF THE INVENTION

This invention relates to prodrugs of oxazolidinone compounds which are CETP inhibitors.

BACKGROUND OF THE INVENTION

Atherosclerosis and its clinical consequences, coronary heart disease (CHD), stroke and peripheral vascular disease, represent a truly enormous burden to the health care systems of the industrialized world. In the United States alone, approximately 13 million patients have been diagnosed with CHD, and greater than one half million deaths are attributed to CHD each year. Further, this toll is expected to grow over the next quarter century as the average age of the population increases and as an epidemic in obesity and diabetes continues to grow.

Inhibition of cholesterol ester transfer protein (CETP) is a potential new approach to reducing the incidence of atherosclerosis. Statins, which are widely used to help control cholesterol, are effective in reducing LDL-cholesterol (the "bad cholesterol") in patients, and are relatively less effective in raising HDL-cholesterol ("the good cholesterol"). CETP inhibitors are effective in raising HDL-cholesterol and may also reduce LDL-cholesterol. CETP inhibitors therefore represent a potential new tool for controlling lipids and for treating or reducing CHD and atherosclerosis in the general population, either alone or in combination with a statin. A combination of a CETP inhibitor and a statin may be especially advantageous in controlling lipids by raising HDL-C and reducing LDL-C.

Pfizer's torcetrapib is the only CETP inhibitor that has so far been tested in a large-scale clinical trial. The trial (named ILLUMINATE) was stopped before its scheduled completion date, because the patients being treated with torcetrapib and atorvastatin in combination had a higher incidence of mortality than the control group, which was being treated only with atorvastatin. Data generated after the termination of the ILLUMINATE trial using animal studies and further data analysis suggest that the higher incidence of mortality in the patient group treated with torcetrapib may have been due to off-target effects of the molecule rather than the mechanism of action. Studies of other CETP inhibitors are therefore expected to occur, and new compounds are still being investigated. Studies of two CETP inhibitors, dalcetrapib and anacetrapib, are starting or are in progress.

CETP inhibitors are generally lipophilic, having poor solubility in water and in aqueous bodily fluids. Oral formulations of the poorly soluble CETP inhibitors using conventional tablet formulations have limited aqueous solubility and generally exhibit a "food effect," whereby the amount of drug that is absorbed varies, depending on whether the patient takes the drug with a meal or in a fasted state. Efforts have been made to develop formulations that have better bioavailability. A potent class of substituted oxazolidinones, imidazolidinones, and other similar 5-membered heterocycles (see WO 2006/014357 and WO 2006/014413) was recently disclosed. As was observed with other CETT' inhibitors, the compounds have poor water solubility. A particularly active compound that is disclosed in these applications is anacetrapib, which is the oxazolidinone compound pictured herein as compound III. Liquid formulations of the oxazolidinone compounds in surfactants (WO2007/067593) and solid formulations of the oxazolidinone compounds in water soluble polymers (WO2007/092642) have been developed that provide improved solubility and bioavailability compared with conventional formulations of the drugs.

This application discloses an alternative approach to improving the oral availability of the drugs. Prodrugs are disclosed which are easy to administer and which are converted to the active drug in vivo. With the prodrugs of the oxazolidinone compounds that are described in this application, the oxazolidinone ring is formed by a cyclization reaction which forms the active drug after administration to a patient. A somewhat analogous approach has been disclosed in which a 5-membered heterocycle is produced as a by-product of a coupling reaction: W. S. Saari et al., *J. Med. Chem.*, 1990, 33, pp. 97-101.

SUMMARY OF THE INVENTION

The present invention provides a prodrug having formula I:

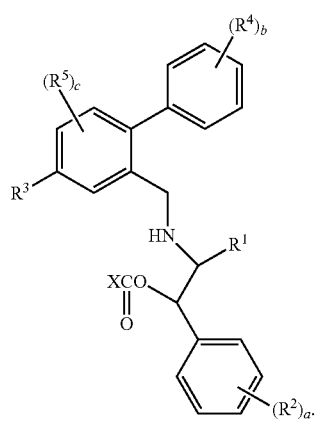

The compound of Formula I is a prodrug which readily converts to the compound having Formula II when it is administered to a patient. The prodrug is most often administered orally, though other routes of administration may also be used. The prodrug converts to the active drug during or after administration, generally after administration. The compound of formula I is converted to the active oxazolidinone compound of formula II by a cyclization reaction or reactions in which the N and carbonyl are joined together to form the 5-membered oxazolidinone ring of the compound of formula II.

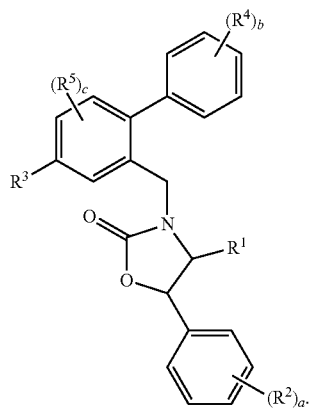

In the compounds having Formula I and Formula II:

$R^1$ is H or $C_{1-4}$alkyl, which is optionally substituted with 1-5 F groups;

Each $R^2$ is independently selected from the group consisting of halogen, —CN, $C_{1-4}$alkyl, and —$OC_{1-4}$alkyl, wherein $C_{1-4}$alkyl and —$OC_{1-4}$alkyl are optionally substituted with 1-5 halogens;

$R^4$ and $R^5$ are each independently selected from the group consisting of halogen, $C_{1-4}$alkyl, and —$OC_{1-4}$alkyl, wherein $C_{1-4}$alkyl and —$OC_{1-4}$alkyl are optionally substituted with 1-5 halogens;

$R^3$ is selected from H, halogen, $C_{1-4}$alkyl, and —$OC_{1-4}$alkyl, wherein $C_{1-4}$alkyl and —$OC_{1-4}$alkyl are optionally substituted with 1-5 halogens;

a and b are integers which are each independently selected from 0-4; and c is an integer from 0-2.

In the prodrug of Formula I, X is a leaving group which is displaced by the N during the cyclization reaction in which I is converted to II.

X has the structure —OZ or —SZ, wherein:

Z is selected from (a) $C_1$-$C_5$ alkyl which optionally includes an —O— atom between 2 adjacent carbon atoms, wherein said $C_1C_5$ alkyl is optionally substituted with 1-5 halogens and is optionally substituted with 1-2 substituent groups independently selected from phenyl, —C(=O)$OR^6$, —OP(=O)$(OR^7)_2$, and —P(=O)$(OR^7)_2$, wherein phenyl is optionally substituted with 1-3 groups independently selected from halogen, —C(=O)$OR^7$, and $C_1$-$C_3$alkyl optionally substituted with 1-3 halogens; and (b) phenyl, wherein phenyl is optionally substituted with 1-3 groups independently selected from halogen; $C_1$-$C_5$alkyl; —$OC_1$-$C_5$alkyl; —C(=O)$OR^7$; and $C_5$-$C_7$cycloalkyl optionally substituted with 1-2 groups independently selected from halogen, $C_1$-$C_3$alkyl, —$OC_1$-$C_3$alkyl, $CF_3$, and —$OCF_3$; wherein $C_1$-$C_5$alkyl and —$OC_1$-$C_5$alkyl are optionally substituted with 1-5 F and are optionally substituted with 1-2 groups independently selected from —C(=O)$OR^7$, —N$(R^7)_2$, —OP(=O)$(OR^7)_2$, and —P(=O)$(OR^7)_2$;

$R^6$ is selected from H and $C_1$-$C_5$ alkyl which is optionally substituted with 1-5 halogens and is optionally substituted with 1-2 phenyl groups wherein phenyl is optionally substituted with 1-3 groups independently selected from halogen, $C_1$-$C_3$ alkyl, —$OC_1$-$C_3$ alkyl, $CF_3$, and —$OCF_3$; and $R^7$ is selected from H and $C_1$-$C_3$ alkyl optionally substituted with 1-3 F.

DETAILED DESCRIPTION OF THE INVENTION

In embodiments of the compounds of Formula I and II described above, $R^1$ is H or $C_{1-3}$ alkyl, optionally substituted with 1-5 F. $R^1$ in preferred embodiments is $C_{1-2}$ alkyl, optionally substituted with 1-3 F. In other preferred embodiments, $R^1$ is $C_{1-2}$ alkyl. In other preferred embodiments, $R^1$ is $CH_3$.

In embodiments of the compound of Formula I and II, each $R^2$ is independently selected from —CN, F, $C_{1-3}$alkyl optionally substituted with 1-5 F, and —$OC_{1-3}$alkyl optionally substituted with 1-5 F. In other embodiments, each $R^2$ is independently selected from —CN, F, $C_{1-3}$alkyl optionally substituted with 1-5 F, and —$OC_{1-2}$alkyl optionally substituted with 1-5F. In preferred embodiments, each $R^2$ is independently selected from —CN, $C_{1-3}$alkyl, $CF_3$, —$OCH_3$, —$OCF_3$, and F.

In other preferred embodiments, each $R^2$ is independently selected from —CN, $CH_3$ and $CF_3$. In other preferred embodiments, each $R^2$ is $CH_3$ or $CF_3$. And in other preferred embodiments, $R^2$ is $CF_3$.

In embodiments of the compound of Formula I and II, $R^4$ and $R^5$ are each independently selected from F, $C_{1-3}$alkyl optionally substituted with 1-5 F, and —$OC_{1-3}$alkyl optionally substituted with 1-5 F. In other embodiments, $R^4$ and $R^5$ are each independently selected from F, $C_{1-3}$alkyl optionally substituted with 1-5 F, and —$OC_{1-2}$alkyl optionally substituted with 1-5F. In other embodiments, $R^4$ and $R^5$ are each independently selected from $C_{1-3}$alkyl, $CF_3$, —$OCH_3$, —$OCF_3$, and F.

In preferred embodiments, each $R^4$ is independently selected from $C_{1-3}$alkyl, $CF_3$, —$OCH_3$, —$OCF_3$, and F. In other preferred embodiments, each $R^4$ is independently selected from $C_{1-3}$alkyl, $CF_3$, —$OCH_3$, and F. In other preferred embodiments, each $R^4$ is independently selected from $C_{1-3}$alkyl, —$OCH_3$, and F.

In embodiments, $R^3$ is $C_{1-3}$alkyl, —$OC_{1-3}$alkyl, or F, wherein $C_{1-3}$alkyl and $OC_{1-3}$alkyl are optionally substituted with 1-5 F.

In preferred embodiments, $R^3$ is $CH_3$, $CF_3$ or F.

In other preferred embodiments, $R^3$ is $CF_3$.

In preferred embodiments, a is 1 or 2. In other preferred embodiments, a is 2.

In preferred embodiments, b is an integer from 1-3. In other preferred embodiments, b is 2 or 3. In other preferred embodiments, b is 3.

In preferred embodiments c is 0 or 1. In other preferred embodiments, c is 0.

In some embodiments, Z is selected from (a) $C_1$-$C_5$ alkyl which optionally includes an —O—atom between 2 adjacent carbon atoms, wherein said $C_1$-$C_5$ alkyl is optionally substituted with 1-3 F and is optionally substituted with 1-2 substituent groups independently selected from phenyl, —C(=O)$OR^6$, —OP(=O)$(OR^7)_2$, and —P(=O)$(OR^7)_2$, wherein phenyl is optionally substituted with 1-3 groups independently selected from halogen, $C_1$-$C_3$alkyl, $CF_3$, and —C(=O)$OR^7$; and (b) Phenyl, wherein phenyl is optionally substituted with 1-3 groups independently selected from halogen; $C_1$-$C_5$alkyl; $CF_3$; —$OC_1$-$C_3$alkyl; —$OCF_3$; —C(=O)$OR^7$; and $C_5$-$C_6$cycloalkyl which is optionally substituted with 1-2 groups independently selected from halogen, $CH_3$, and —$OCH_3$; wherein $C_1$-$C_5$alkyl and —$OC_1$-$C_3$alkyl are optionally substituted with 1-2 groups independently selected from —C(=O)$OR^7$, —N$(R^7)_2$, —OP(=O)$(OR^7)_2$; and —P(=O)$(OR^7)_2$.

In some embodiments, $R^6$ is selected from H and $C_1$-$C_2$alkyl which is optionally substituted with one phenyl group, said phenyl being optionally substituted with 1-3 groups independently selected from halogen, $CH_3$, $CF_3$, —$OCH_3$, and —$OCF_3$.

In some embodiments, $R^7$ is selected from H and $C_1$-$C_3$ alkyl optionally substituted with 1-3 F.

In some embodiments, X is selected from —$SC_1$-$C_3$alkyl and —OZ. In some embodiments, X is selected from —$SC_1$-$C_2$alkyl and —OZ.

In some embodiments, X is —$SC_1$-$C_2$alkyl. In some embodiments, X is —OZ.

In some embodiments, Z is selected from (a) —$(CH_2CH_2O—)_nC_1$-$C_3$alkyl, where n is 0 or 1, and wherein $C_1$-$C_3$alkyl is optionally substituted with 1-2 substituent groups independently selected from phenyl, —C(=O)OR⁶, —OP(=O)(OR⁷)₂, and —P(=O)(OR⁷)₂, wherein phenyl is optionally substituted with one group —C(=O)OR⁷; and (b) phenyl, which is optionally substituted with 1-3 substituents independently selected from $C_1$-$C_4$ alkyl, —O$C_1$-$C_3$alkyl, —C(=O)OR⁷, and cyclohexyl, wherein $C_1$-$C_4$ alkyl and —O$C_1$-$C_3$alkyl are optionally substituted with 1-2 groups independently selected from —N(R⁷)₂, —C(=O)OR⁷, and —OP(=O)(OR⁷)₂.

In some embodiments, Z is selected from the group consisting of:

(a) —(CH₂CH₂O—)$_n$$C_1$-$C_3$alkyl, wherein $C_1$-$C_3$alkyl is optionally substituted with 1-2 substituent groups independently selected from phenyl, —C(=O)OR⁶, —OP(=O)(OR⁷)₂, and —P(=O)(OR⁷)₂, wherein phenyl is optionally substituted with one group —C(=O))OR⁷; and (b) phenyl, which is substituted with 1-3 substituents independently selected from $C_1$-$C_4$ alkyl, —O$C_1$-$C_3$alkyl, —C(=O)OR⁷, and cyclohexyl, wherein $C_1$-$C_4$alkyl and —O$C_1$-$C_3$alkyl are optionally substituted with 1-2 groups independently selected from —N(R⁷)₂, —C(=O)OR⁷, and —OP(=O)(OR⁷)₂.

In some embodiments, R⁶ is selected from H, $C_1$-$C_2$alkyl, and —CH₂phenyl.

In some embodiments, R⁷ is selected from H and $C_1$-$C_2$alkyl.

A particularly preferred embodiment of this invention is directed to prodrugs for making the compound having formula III, including pharmaceutically acceptable salts thereof:

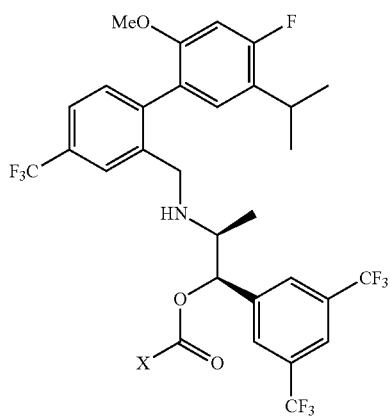

III

The prodrug that is converted to Compound III when it is administered to a patient has the formula IV, shown below, where X is as defined previously.

IV

Utility

The prodrugs of Formula I and IV described above chemically eliminate the oxazolidinone-based drug under buffered conditions at a pH in the range of 7.0-8.0, and preferably at about 7.5, and at a temperature of about 37° C. (in the range of about 36-38° C.). These conditions are representative of the conditions that occur in the small intestine shortly after the contents of the stomach pass from the stomach into the small intestine. The drugs that are produced by the cyclization reactions, compounds II and III, are potent inhibitors of CETP in humans and animals, and have been shown to raise HDL-cholesterol and reduce LDL-cholesterol in humans and in animals that have CETP genes. The compounds are expected to have utility in the treatment and prevention of atherosclerosis and associated diseases and disorders.

The compounds and the formulations of the compounds are useful in treating diseases which are characterized by low-HDL and/or high-LDL, or which can be treated or ameliorated by raising HDL and/or reducing LDL such as hypercholesterolemia, hyperlipidemia, and atherosclerosis. Furthermore, administration of the compounds and formulations described herein does not cause an increase in blood pressure as was observed for torcetrapib.

Doses of the prodrug in humans that will be therapeutically effective in raising HDL and lowering LDL are the amounts that are equivalent after cyclization to active drug in an amount in the range of 20 mg to 200 mg, such as for example 20 mg, 25 mg, 30 mg, 40 mg, 50 mg, 60 mg, 70 mg, 80 mg, 90 mg, 100 mg, 110 mg, 120 mg, 130 mg, 140 mg, 150 mg, 160 mg, 180 mg and 200 mg, administered once or twice a day, but preferably once a day. A preferred dose will provide 100 mg of active drug and will be administered once a day.

The prodrugs provide improved bioavailability compared with conventional formulations of the active drug. Furthermore, conventional formulations comprising the CETP inhibitors that are made from the prodrugs herein exhibit a "food effect," which results in differences in the amount and rate of absorption into the body depending on when the patient was last fed, how soon the patient eats after oral administration of the drug, and whether the patient takes the drug before a meal, with a meal, or after a meal. The prodrug formulations disclosed herein should exhibit a reduced food effect compared with conventional formulatons because they cyclize to the active drug after the prodrug has passed into the small intestine, which is the site of absorption.

EXAMPLES

The following examples are provided to more fully illustrate the invention and are not to be construed as limiting the scope of the invention, which is defined only by the appended claims.

INTERMEDIATE 1

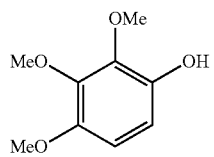

2,3,4-Trimethoxyphenol

A solution of 2,3,4-trimethoxybenzaldehyde (1.00 g, 5.10 mmol) and 30 wt/v % hydrogen peroxide (0.672 mL, 6.52 mmol) in conc. H₂SO₄ (0.102 mL) and MeOH (10.19 mL) was stirred overnight at 25° C. under N₂. After this time the mixture was diluted with water (20 mL) and extracted with CH$_2$Cl$_2$ (3×30 mL). The combined extracts were dried (MgSO$_4$) and concentrated in vacuo to afford the crude product. This was purified by flash chromatography (Biotage Horizon, 40M, Si, ~30 mL/min, 100% hexanes for 360 mL, gradient to 50% EtOAc in hexanes over 2088 mL) to afford 2,3,4-trimethoxyphenol, as a colorless oil. R$_f$=0.93 (50% EtOAc/hexanes). LCMS calc.=185.1; found=185.2 (M+H)$^+$. $^1$H NMR (600 MHz, CDCl$_3$): δ 6.62 (d, J=9.0 Hz, 1 H); 6.55 (d, J=8.9 Hz, 1 H); 5.49 (s, 1 H); 3.94 (s, 3 H); 3.89 (s, 3 H); 3.80 (s, 3 H).

The intermediates described in Table 1 were prepared using methods analogous to those described for INTERMEDIATE 1 starting from commercially available benzaldehydes.

TABLE 1

| Intermediate | Structure | LCMS (M + H)+ |
|---|---|---|
| 2 | 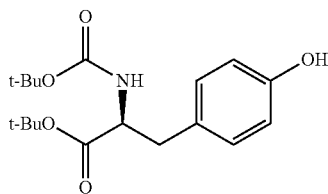 | 155.0 |
| 3 | 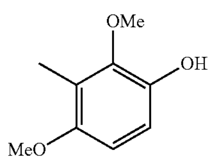 | 169.1 |

INTERMEDIATE 4 tert-Butyl (2S)-2-[(tert-butoxycarbonyl)amino]-3-(4-hydroxyphenyl)propanoate

A solution of di-tort-butyl dicarbonate (6.81 g, 31.2 mmol) in dry CH$_2$Cl$_2$ (15 mL) was added dropwise via cannula to a stirred solution of L-tyrosine tert-butyl ester (6.17 g, 26.0 mmol) and triethylamine (5.26 g, 7.25 mL, 52.0 mmol) at 0° C. under N$_2$. The reaction was stirred at room temperature overnight. Water (30 mL) was added and the mixture was stirred for 30 min. The organic layer was washed with water (20 mL), 0.05 M HCl (20 mL), water (20 mL) and brine (20 mL), dried (MgSO$_4$) and concentrated in vacuo to give the crude product. This was purified by flash chromatography (Biotage Horizon, 65i, Si, ~70 mL/min, 100% hexanes for 450 mL, gradient to 25% EtOAc in hexanes over 4446 mL, gradient to 40% EtOAc in hexanes over 2448 mL) to afford tert-butyl (2S)-2-[(tert-butoxycarbonyl)amino]-3-(4-hydroxyphenyepropanoate. R$_f$=0.28 (20% EtOAc/hexanes). LCMS calc.=360.2; found=359.9 (M+Na)$^+$. $^1$H NMR (500 MHz, CDCl$_3$): δ 7.02 (d, J=8.1 Hz, 2 H); 6.73 (d, J=8.1 Hz, 2 H); 5.41 (s, 1 H); 4.99 (d, J=7.9 Hz, 1 H); 4.40 (q, J=6.6 Hz, 1 H); 3.01-2.93 (m, 2 H); 1.42 (s, 9 H); 1.41 (s, 9 H).

INTERMEDIATE 5

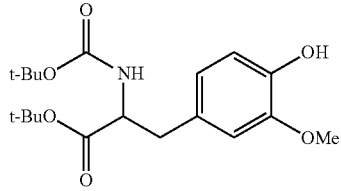

tert-Butyl 2-[(tert-butoxycarbonyl)amino]-3-(4-hydroxy-3-methoxyphenyl)propanoate Step A: 2-[(tert-Butoxycarbonyl)amino]-3-(4-hydroxy-3-methoxyphenyl)propanoic acid Triethylamine (719 mg, 980 μL, 7.10 mmol) was added to a solution of 3-methoxy-DL-tyrosine (1.00 g, 4.73 mmol) in 1,4-dioxane/water (1:1, 17.2 mL). The solution was cooled to 0° C. and di-tert-butyl dicarbonate (1.14 g, 5.21 mmol) was added in one batch. The reaction was warmed to room temperature and stirred for 3 days. The reaction mixture was concentrated in vacuo and the residue was diluted with water and EtOAc. The aqueous layer was washed with EtOAc, acidified to pH 1 with 1N HCl and back extracted with EtOAc. The combined organic extracts were dried (MgSO$_4$) and concentrated in vacuo to afford 2-[(tert-butoxycarbonyl)amino]-3-(4-hydroxy-3-methoxyphenyl)propanoic acid, as an off-white solid. LCMS calc.=334.1; found=333.8 (M+Na)$^+$. $^1$H NMR (500 MHz, CDCl$_3$): δ 6.77-6.67 (m, 3 H); 5.28 (d, J=7.2 Hz, 1 H); 4.39 (dd, J=5.8, 12.4 Hz, 1 H); 3.83 (s, 3 H); 3.12 (dd, J=5.3, 13.8 Hz, 2 H); 1.41 (s, 9 H); 1.35 (s, 1 H).

Step B: tert-Butyl 2-[(tert-butoxycarbonyl)amino]-3-(4-hydroxy-3-methoxyphenyl)propanoate t-BuOH (5.17 g, 6.67 mL, 69.8 mmol) was added to a stirred suspension of 2-[(tert-butoxycarbonyl)amino]-3-(4-hydroxy-3-methoxyphenyl)propanoic acid (1.55 g, 4.98 mmol) in dry toluene (25 mL). The mixture was brought to reflux to give a homogeneous solution. N,N-dimethylformamide dineopentyl acetal (3.46 g, 4.17 mL, 15.0 mmol) was added dropwise over 1 h at reflux. After heating at reflux to 3-4 h, the reaction mixture was cooled to room temperature and a saturated solution of NaHCO$_3$ (40 mL) was added. The mixture was extracted with CH$_2$Cl$_2$ (3×40 mL) and the combined extracts were dried (Na$_2$SO$_4$) and concentrated in vacuo to give the crude product. This was purified by flash chromatography (Biotage Horizon, 40M, Si, ~30 mL/min, 100% hexanes for 360 mL, gradient to 20% EtOAc in hexanes over 4536 mL) to afford tert-butyl 2-[(tert-butoxycarbonyl) amino]-3-(4-hydroxy-3-methoxyphenyl)propanoate. R$_f$=0.42 (20% EtOAc/hexanes). LCMS calc.=390.2; found=389.9 (M+Na)$^+$. $^1$H NMR (500 MHz, CDCl$_3$): δ 6.82 (d, J=7.9 Hz, 1 H); 6.87-6.63 (m, 2 H); 5.54 (s, 1 H); 4.97 (d, J=7.8 Hz, 1 H); 4.40 (q, J=6.7 Hz, 1 H); 3.86 (s, 3 H); 2.98 (d, J=6.0 Hz, 2 H); 1.42 (s, 9 H); 1.41 (s, 9 H).

INTERMEDIATE 6

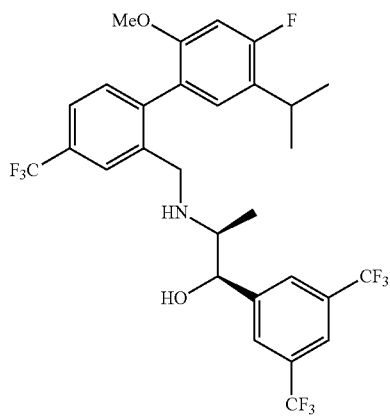

(1R,2S)-1-[3,5-Bis(trifluoromethyl)phenyl]-2-({[4'-fluoro-5'-isopropyl-2'-methoxy-4-(trifluoromethyl)biphenyl-2-yl]methyl}amino)propan-1-ol Potassium hydroxide (368.3 mg, 6.56 mmol) was added to a stirred solution of (4S,5R)-5-[3,5-bis(trifluoromethyl)phenyl]-3-{[4'-fluoro-5'-isopropyl-2'-methoxy-4-(trifluoromethyl)biphenyl-2-yl]methyl}-4-methyl-1,3-oxazolidin-2-one (0.87 g, 1.36 mmol) in i-PrOH (44.7 mL) and water (9.0 mL) and the mixture was heated at 75° C. in a sealed tube overnight. The reaction was cooled to room temperature and concentrated in vacuo to remove most of the i-PrOH. Brine (25 mL) was added and the mixture was extracted with EtOAc (3×50 mL). The combined extracts were dried (MgSO$_4$) and concentrated in vacuo to afford (1R,2S)-1-[3,5-bis(trifluorormethyl)phenyl]-2-({[4'-fluoro-5'-isopropyl-2'-methoxy-4-(trifluoromethyl)biphenyl-2-yl]methyl}amino)propan-1-ol, as a colorless solid. $R_f$=0.49 (20% EtOAc/hexanes). LCMS calc.=612.2; found=611.8 (M+H)$^+$. $^1$H NMR (500 MHz, CDCl$_3$): δ 7.76-7.69 (m, 4 H); 7.60 (d, J=7.8 Hz, 1 H); 7.33 (dd, J=4.0, 7.9 Hz, 1 H); 7.00 (d, J=8.5 Hz, 1 H); 6.71 (dd, J=5.9, 11.9 Hz, 1 H); 4.74 (br d, J=16.0 Hz, 1 H); 3.85-3.70 (m, 6 H); 3.26-3.18 (m, 1 H); 2.81-2.78 (m, 1 H); 1.28-1.20 (m, 7 H); 0.62 (d, J=6.5 Hz, 3 H).

INTERMEDIATE 7

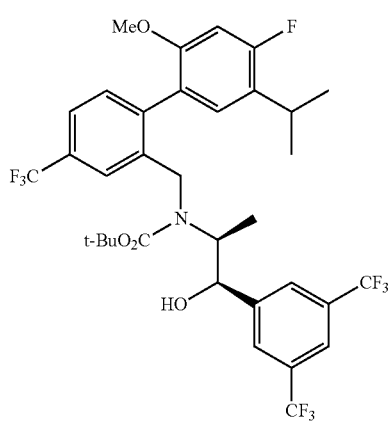

tert-Butyl {(1S,2R)-2-[3,5-bis(trifluoromethyl)phenyl]-2-hydroxy-1-methylethyl}{[4'-fluoro-5'-isopropyl-2'-methoxy-4-(trifluoromethyl)biphenyl-2-yl]methyl}carbamate Diisopropylethylamine (363 mg, 489 µL, 2.81 mmol) was added to a stirred solution of (1R,2S)-1-[3,5-bis(trifluoromethyl)phenyl]-2-({[4'-fluoro-5'-isopropyl-2'-methoxy-4-(trifluoromethyl)biphenyl-2-yl]methyl}amino)propan-1-ol (858 mg, 1.40 mmol) in dry MeCN (16 mL) at room temperature under N$_2$. The resulting solution was cooled to 0° C. and di-tert-butyldicarbonate (337 mg, 1.54 mmol) was added. The resulting mixture was warmed to room temperature and stirred for 2 days. The reaction mixture was diluted with Et$_2$O (20 mL) and washed with water (10 mL) and brine (10 mL), dried (MgSO$_4$) and concentrated in vacuo to give the crude product. This was purified by flash chromatography (Biotage Horizon, 25M, Si, ~20 mL/min, 100% hexanes for 144 mL, gradient to 20% EtOAc in hexanes over 2880 mL) to afford tert-butyl {(1S,2R)-2-[3,5-bis(trifluoromethyl)phenyl]-2-hydroxy-1-methylethyl}{[4'-fluoro-5'-isopropyl-2'-methoxy-4-(trifluoromethyl)biphenyl-2-yl]methyl}carbamate, as a colorless solid. $R_f$=0.63 (20% EtOAc/hexanes). LCMS calc.=734.2; found=733.9 (M±Na)$^+$.

INTERMEDIATE 8

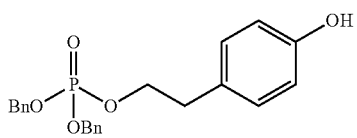

Dibenzyl 2-(4-hydroxyphenyl)ethyl phosphate

Step A: 4-(2-Bromoethyl)phenyl acetate

Acetyl chloride (2.01 g, 1.82 mL. 25.6 mmol) was added to a stirred solution of pyridine (2.02 g, 2.07 mL, 25.6 mmol) and 4-hydroxyphenethyl bromide (856.5 mg, 4.26 mmol) in dry CH$_2$Cl$_2$ (17 mL) and the reaction was stirred at room temperature for 2 h. The reaction mixture was diluted with water (20 mL) and extracted with CH$_2$Cl$_2$ (2×40 mL). The combined extracts were dried (MgSO$_4$) and concentrated in vacuo to afford 4-(2-bromoethyl)phenyl acetate. $^1$H NMR (500 MHz, CHCl$_3$): δ 7.22 (d, J=8.3 Hz, 2 H); 7.04 (d, J=8.3 Hz, 2 H); 3.55 (t, J=7.6 Hz, 2 H); 3.16 (t, J=7.6 Hz, 2 H); 2.29 (s, 3 H).

Step B: 4-(2-{[Bis(benzyloxy)phosphoryl]oxy}ethyl)phenyl acetate

Silver dibenzylphosphate (2.08 g, 5.39 mmol) was added to a stirred solution of 4-(2-bromoethyl)phenyl acetate (1.31 g, 5.39 mmol) in toluene (43 mL) and the mixture was heated at reflux overnight. The precipitate formed was removed by filtration through a plug of Celite. The filter cake was washed with toluene and the combined filtrates were concentrated in vacuo to give the crude product. This was purified by flash chromatography (Biotage Horizon, 40M, Si, ~30 mL/min, 100% hexanes for 360 mL, gradient to 50% EtOAc in hexanes over 4536 mL) to afford 4-(2-{[bis(benzyloxy)phosphoryl]oxy}ethyl)phenyl acetate. $R_f$=0.51 (50% EtOAc/hexanes).

LCMS calc.=441.1; found=440.9 (M+H)$^+$. $^1$H NMR (500 MHz, CHCl$_3$): δ 7.37-7.30 (m, 10 H); 7.15 (d, J=8.3 Hz, 2 H); 6.99 (d, J=8.3 Hz, 2 H); 4.15 (q, J=7.1 Hz, 2 H); 2.89 (t, J=7.0 Hz, 2 H); 2.28 (s, 3 H).

Step C: Dibenzyl 2-(4-hydroxyphenyl)ethyl phosphate

Potassium carbonate (62.8 mg, 0.454 mmol) was added to a stirred solution of 4-(2-{[bis(benzyloxy)phosphoryl] oxy}ethyl)phenyl acetate (100 mg, 0.227 mmol) in MeOH (20.5 mL) at 25° C. The reaction was stirred at 25° C. for 1 h. The reaction mixture was concentrated in vacuo and the resulting residue was partitioned between water (20 mL) and EtOAc (20 mL). The aqueous layer was separated and extracted with EtOAc (2×20 mL). The combined organic extracts were dried (MgSO$_4$) and concentrated in vacuo to afford dibenzyl 2-(4-hydroxyphenyl)ethyl phosphate, as an oil. LCMS calc.=399.1; found=398.9 (M+H)$^+$. $^1$H NMR (500 MHz, CHCl$_3$): δ 8.05 (1 H, s); 7.41-7.30 (m, 10 H); 6.99 (d, J=8.2 Hz, 2 H); 6.86 (d, J=8.3 Hz, 2 H); 5.02 (s, 2 H); 5.00 (s, 2 H); 4.18 (q, J=7.1 Hz, 2 H); 2.86 (t, J=7.1 Hz, 2 H).

INTERMEDIATE 9

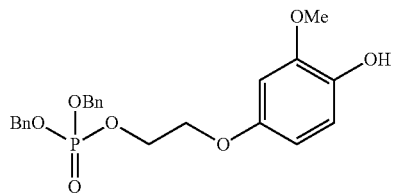

Dibenzyl 2-(4-hydroxy-3-methoxyphenoxy)ethyl phosphate

Step A: 4-(2-Hydroxyethoxy)-2-methoxybenzaldehyde

A solution of 4-hydroxy-2-methoxybenzaldehyde (1.217 g, 8.00 mmol) in dry DMF (8.88 mL) was added to a stirred suspension of sodium hydride (60% dispersion in mineral oil) (0.267 mL, 8.00 mmol) in dry DMF (2.22 mL) via cannula at 0° C. under N$_2$. The reaction mixture was stirred at 0° C. for 30 min and warmed to room temperature. 2-bromoethanol (0.851 mL, 12.00 mmol) was added dropwise and the reaction mixture was stirred at 50° C. overnight. The reaction was diluted with water (50 mL) and extracted with EtOAc (3×50 mL). The combined extracts were washed with 1N aq. NaOH (50 mL), dried (MgSO$_4$) and concentrated in vacuo to afford the crude product. This was purified by flash chromatography (Biotage Horizon, 40M, Si, ~30 mL/min, 100% hexanes for 360 mL, gradient to 60% EtOAc in hexanes over 4536 mL) to afford 4-(2-hydroxyethoxy)-2-methoxybenzaldehyde, as a colorless solid. R$_f$=0.29 (50% EtOAc/hexanes). LCMS calc.=197.1; found=197.0 (M+H)$^+$. $^1$H NMR (500 MHz, CHCl$_3$): δ 10.16 (s, 1 H); 7.68 (d, J=8.7 Hz, 1 H); 6.46 (dd, J=8.7, 2.2 Hz, 1 H); 6.40 (d, J=2.2 Hz, 1 H); 4.09 (t, J=4,6 Hz, 2 H); 3.94 (t, J=4.4 Hz, 2 H); 3.79 (s, 3 H); 3.20 (s, 1 H).

Step B: 4-(2-Hydroxyethoxy)-2-methoxyphenol

A solution of 4-(2-hydroxyethoxy)-2-methoxybenzaldehyde (465.6 mg, 2.373 mmol) and 30 wt % hydrogen peroxide (0.313 mL, 3.04 mmol) in conc. H$_2$SO$_4$ (0.0475 mL) and MeOH (4.75 mL) was stirred overnight at 25° C. under N$_2$. After this time the mixture was diluted with water (20 mL) and extracted with CH$_2$Cl$_2$ (3×30 mL). The combined extracts were dried (MgSO$_4$) and concentrated in vacuo to afford the crude product. This was purified by flash chromatography (Biotage Horizon, 25M, Si, ~20 mL/min, 100% hexanes for 144 mL, gradient to 55% EtOAc in hexanes over 2394 mL, gradient to 100% EtOAc over 999 mL) to afford 4-(2-hydroxyethoxy)-2-methoxyphenol, as a colorless oil. R$_f$=0.30 (50% EtOAc/hexanes). LCMS calc.=207.1; found=206.9 (M+Na)$^+$. $^1$H NMR (500 MHz, CHCl$_3$): δ 6.77 (d, J=8.6 Hz, 1 H); 6.47 (d, J=2.8 Hz, 1 H); 6.34 (dd, J=8.7, 2.8 Hz, 1 H); 5.82 (s, 1 H); 3.98 (t, J=4.6 Hz, 2 H); 3.90 (t, J=4.5 Hz, 2 H); 3.76 (s, 3 H); 2.96 (s, 1 H).

Step C: 4-(2-Hydroxyethoxy)-2-methoxyphenyl acetate

A solution of 1-acetyl-1H-1,2,3-triazolo[4,5-b]pyridine (0.248 g, 1.532 mmol) in dry THF (6.13 mL) was added to a solution of 4-(2-hydroxyethoxy)-2-methoxyphenol (0,2821 g, 1.532 mmol) in 1N aq. NaOH (1.532 mL, 1.532 mmol) at 25° C. The reaction was stirred at 25° C. for 3 h. The reaction was diluted with 1IN HCl (20 mL) and extracted with Et$_2$O (3×20 mL). The combined extracts were dried (MgSO$_4$) and concentrated in vacuo to afford the crude product. This was purified by flash chromatography (Biotage Horizon, 25M, Si, ~20 mL/min, 100% hexanes for 144 mL, gradient to 50% EtOAc in hexanes over 360 mL, gradient to 100% EtOAc over 2034 mL) to afford 4-(2-hydroxyethoxy)-2-methoxyphenyl acetate. R$_f$=0.28 (50% EtOAc/hexanes). LCMS calc.=249.1; found=249.0 (M+Na)$^+$. $^1$H NMR (500 MHz, CHCl$_3$): δ 6.87 (d, J=8.7 Hz, 1 H); 6.52 (d, J=2.7 Hz, 1 H); 6.38 (dd, J=8.7, 2.7 Hz, 1 H); 3.96 (t, J=4.7 Hz, 2 H); 3.84 (t, J=4.7 Hz, 2 H); 3.71 (s, 3 H); 2.97 (s, 1 H); 2.24 (s, 3 H).

Step D: 4-(2-Bromoethoxy)-2-methoxyphenyl acetate

A solution of triphenylphosphine (0.123 mL, 0.530 mmol) in dry CH$_2$Cl$_2$ (1.3 mL) was added dropwise via cannula to a stirred solution of 4-(2-hydroxyethoxy)-2-methoxyphenyl acetate (100 mg, 0.442 mmol) and carbon tetrabromide (0.051 mL, 0.530 mmol) in dry CH$_2$Cl$_2$ (3.0 mL) at 0° C. under N$_2$. After 5 h at 0° C., the reaction mixture was concentrated in vacuo and the residue obtained was purified by flash chromatography (Biotage Horizon, 25M, Si, ~20 mL/min, 100% hexanes for 144 mL, gradient to 50% EtOAc in hexanes over 1125 mL) to afford 4-(2-bromoethoxy)-2-methoxyphenyl acetate, as a colorless oil. R$_f$=0.78 (50% EtOAc/hexanes). LCMS calc.=289.1; found=288.8 (M+H)$^+$. $^1$H NMR (500 MHz, CHCl$_3$): δ 6.93 (d, J=8.7 Hz, 1 H); 6.57 (d, J=2.8 Hz, 1 H); 6.42 (dd, J=8.7, 2.8 Hz, 1 H); 4.26 (t, J=6.2 Hz, 2 H); 3.80 (s, 3 H); 3.62 (t, J=6.2 Hz, 2 H); 2.29 (s, 3 H).

Step E: 4-(2{[Bis(benzyloxy)phosphoryl] oxy}ethoxy)-2-methoxyphenyl acetate

Silver dibenzylphosphate (134 mg, 0.348 mmol) was added to a solution of 4-(2-bromoethoxy)-2-methoxyphenyl acetate (100.6 mg, 0.348 mmol) in toluene (2.762 mL) and the mixture was heated at reflux overnight. The precipitate formed was removed by filtration through a plug of Celite and washed through with toluene. The filtrate was concentrated in vacuo to give the crude product. This was purified by flash chromatography (Biotage Horizon, 20M, Si, ~20 mL/min, 100% hexanes for 144 mL, gradient to 70% EtOAc in hexanes over 1125 mL, gradient to 100% EtOAc over 999 mL) to afford 4-(2-{[bis(benzyloxy)phosphoryl]oxy}ethoxy)-2-methoxyphenyl acetate, as a colorless oil. $R_f$=0.26 (50% EtOAc/hexanes). LCMS calc.=487.2; found=486.9 (M+H)$^+$. $^1$H NMR (500 MHz, CHCl$_3$): δ 7.35-7.31 (m, 10 H); 6.91 (d, J=8.7 Hz, 1 H); 6.50 (d, J=2.7 Hz, 1 H); 6.37 (dd, J=8.7, 2.7 Hz, 1 H); 5.12-5.02 (m, 4 H); 4.33-4.28 (m, 2 H); 4.07 (t, J=4.6 Hz, 2 H); 3.73 (s, 3 H); 2.28 (s, 3 H).

Step F: Dibenzyl 2-(4-hydroxy-3-methoxyphenoxy)ethyl phosphate

Potassium carbonate (0.072 g, 0.524 mmol) was added to a stirred solution of 4-(2-{[bis(benzyloxy)phosphoryl]oxy}ethoxy)-2-methoxyphenyl acetate (0.1274 g, 0.262 mmol) in MeOH (17.5 mL) at 25° C. The reaction was stirred at 25° C. for 1 h. The reaction mixture was concentrated in vacuo and the resulting residue was partitioned between water (20 mL) and EtOAc (20 mL). The aqueous layer was separated and extracted with EtOAc (2×20 mL). The combined organic extracts were dried (MgSO$_4$) and concentrated in vacuo to afford dibenzyl 2-(4-hydroxy-3-methoxyphenoxy)ethyl phosphate, as an oil. LCMS calc.=445.1; found=444.9 (M+H)$^+$.

INTERMEDIATE 10

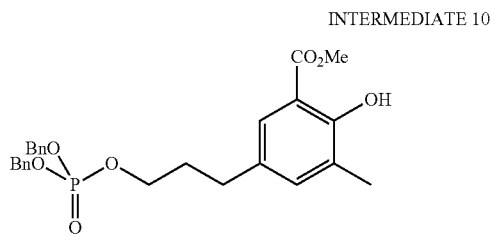 [SMILES: COC(=O)c1cc(CCCOP(=O)(OCc2ccccc2)OCc2ccccc2)cc(C)c1O]

Methyl 5-(3-{[bis(benzyloxy)phosphoryl]oxy}propyl)-2-hydroxy-3-methylbenzoate

Step A: Methyl 2-hydroxy-5-iodo-3-methylbenzoate

Methyl 2-hydroxy-3-methylbenzoate (0.869 g, 5.23 mmol) in MeOH (5 mL) was added dropwise to a suspension of iodine (1.327 g, 5.23 mmol) and silver sulfate (1.63 g, 5.23 mmol), at room temperature under N$_2$. The resultant brown suspension was stirred for 3 h after which time a colorless suspension was observed. The mixture was filtered through a plug of Celite, washed with MeOH (30 mL) and concentrated in vacuo to afford methyl 2-hydroxy-5-iodo-3-methylbenzoate, as a colorless solid. LCMS calc.=292.1; found=292.7 (M+H)$^+$. $^1$H NMR (500 MHz, CHCl$_3$): δ 11.0 (s, 1 H); 8.02 (s, 1 H); 7.62 (s, 1 H); 3.97 (s, 3 H); 2.25 (s, 3 H).

Step B: Methyl 2-(acetyloxy)-5-iodo-3-methylbenzoate

To a stirred suspension of 2-hydroxy-5-iodo-3-methylbenzoate (1.24 g, 4.25 mmol) in neat acetic anhydride (1.803 mL, 19.10 mmol) was added a 3 drops of concentrated sulfuric acid (0.226 mL, 4.25 mmol). The resultant orange solution was stirred at room temperature overnight. The solution was diluted with 3% aqueous NaHCO$_3$ (13 mL) and extracted with CHCl$_3$ (3×30 mL). The combined organic phases were washed with water (4×20 mL), dried (MgSO$_4$), and concentrated in vacuo to afford methyl 2-(acetyloxy)-5-iodo-3-me-thylbenzoate, as a colorless solid. $^1$H NMR (500 MHz, CHCl$_3$): δ 8.17 (s, 1 H); 7.78 (s, 1 H); 3.89 (s, 3 H); 2.25 (s, 3 H); 2.21 (s, 3 H).

Step C: Methyl 2-(acetyloxy)-5-(3-hydroxyprop-1-yn-1-yl)-3-methylbenzoate

Triethylamine (0.943 mL, 6.76 mmol) and bis(triphenylphosphine)palladium(II) chloride (0.092 g, 0.132 mmol) were added to a mixture of methyl 2-(acetyloxy)-5-iodo-3-methylbenzoate (1.0 g, 2.99 mmol) and propargyl alcohol (0.161 mL, 2.69 mmol) in THF (20 mL) at room temperature, and then copper (I) iodide (0.053 g, 0.278 mmol) was added. The resulting mixture was stirred at room temperature for 18 h. The reaction was quenched with water (20 mL) and extracted with EtOAc (3×30 mL). The combined organic extracts were washed with water (50 mL), brine (40 mL), dried (MgSO$_4$), and concentrated in vacuo to give the crude product. This was purified by flash chromatography (Si, 0-20% EtOAc in hexanes over 30 min) to afford methyl 2-(acetyloxy)-5-(3-hydroxyprop-1-yn-1-yl)-3-methylbenzoate, as a yellow solid. $^1$H NMR (500 MHz, CHCl$_3$): δ 7.97 (s, 1 H); 7.53 (s, 1 H); 4.91 (s, 2 H); 3.88 (s, 3 H); 2.22 (s, 3 H); 2.16 (s, 3 H).

Step D: Methyl 2-(acetyloxy)-5-[(1Z)-3-hydroxyprop-1-en-1-yl]-3-methylbenzoate

A suspension of methyl 2-(acetyloxy)-5-(3-hydroxyprop-1-yn-1-yl)-3-methylbenzoate (0.417 g, 1.590 mmol) and palladium on carbon (170 mg, 1.597 mmol) in EtOAc (20 mL) was stirred at room temperature under a balloon atmosphere of H$_2$ for 3 days. The reaction mixture was filtered through a plug of Celite and washed through with EtOAc (3×30 mL). The filtrate was concentrated in vacuo to give the crude product. This was purified by flash chromatography (Si, 0-20% EtOAc in hexanes over 40 min) to afford methyl 2-(acetyloxy)-5-[(1Z)-3-hydroxyprop-1-en-1-yl]-3-methylbenzoate, as a pale yellow oil. $^1$H NMR (500 MHz, CHCl$_3$): δ 7.69 (s, 1 H); 7.29 (s, 1 H); 6.53 (d, J=12 Hz, 1 H); 5.94 (m, 1 H); 4.44 (d, J=6.4 Hz, 2 H); 3.88 (s, 3 H); 2.40 (s, 3 H); 2.25 (s, 3 H).

Step E: Methyl 2-(acetyloxy)-5-(3-hydroxypropyl)-3-methylbenzoate

A suspension of 10% palladium on carbon (146 mg, 0.137 mmol) in a solution of methyl 2-(acetyloxy)-5-[(1Z)-3-hydroxyprop-1-en-1-yl]-3-methylbenzoate (362 mg, 1.370 mmol) in EtOAc (17.2 mL) was shaken in a Parr shaker under H$_2$ at 40 psi overnight. The reaction mixture was filtered through a plug of Celite and washed through with EtOAc. The filtrate was concentrated in vacuo to afford the crude product. This was purified by flash chromatography (Biotage Horizon, 25M, Si, ~20 mL/min, 100% hexanes for 144 mL, gradient to 60% EtOAc in hexanes over 1125 mL) to afford methyl 2-(acetyloxy)-5-(3-hydroxypropyl)-3-methylbenzoate, as a colorless oil. LCMS calc.=289.1; found=288.9 (M+Na)$^+$. $^1$H NMR (500 MHz, CHCl$_3$): δ 7.65 (d, J=2.2 Hz, 1 H); 7.25 (d, J=2.2 Hz, 1 H); 3.84 (s, 3 H); 3.64 (t, J=6.4 Hz, 2 H); 2.67 (t, J=7.8 Hz, 2 H); 2.35 (s, 3 H); 2.18 (s, 3 H); 1.89-1.82 (m, 2 H).

Step F: Methyl 2-(acetyloxy)-5-(3-{[bis(benzyloxy) phosphoryl]oxy}propyl)-3-methylbenzoate Dibenzyl N,N-diisopropylphosphoramidite (0.252 mL, 0.751 mmol) was added to a stirred solution of 1H-tetrazole (3 wt % in $CH_3CN$) (4.40 mL, 1.502 mmol) and methyl 2-(acetyloxy)-5-(3-hydroxypropyl)-3-methylbenzoate (100 mg, 0.376 mmol) in dry $CH_2Cl_2$ (4.50 mL) at 25° C. under $N_2$. The reaction was stirred for 2 h at 25° C. After this time another 0.5 eq dibenzyl N,N-diisopropylphosphoramidite was added and the reaction was stirred for 30 min. The reaction mixture was cooled to 0° C. and a solution of 3-chloroperoxybenzoic acid (337 mg, 1.502 mmol) in dry $CH_2Cl_2$ (3.00 mL) was added via cannula. After 30 min another 1 eq 3-chloroperoxybenzoic acid was added and the reaction was stirred at 0° C. After 30 min the reaction was diluted with EtOAc (30 mL) and washed with successive portions of saturated $Na_2SO_3$ (20 mL) and saturated $NaHCO_3$ (20 mL), dried ($MgSO_4$) and concentrated in vacuo to give the crude product. This was purified by flash chromatography (Biotage Horizon, 25M, Si, ~20 mL/min, 100% hexanes for 144 mL, gradient to 60% EtOAc in hexanes over 2394 mL) to afford methyl 2-(acetyloxy)-5-(3-{[bis(benzyloxy)phosphoryl]oxy}propyl)-3-methylbenzoate, as a colorless oil. LCMS calc.=527.2; found=527.0 (M+H)$^+$. $^1$H NMR (500 MHz, $CHCl_3$): δ 7.62 (d, J=2.2 Hz, 1 H); 7.36-7.31 (m, 10 H); 7.18 (d, J=2.2 Hz, 1 H); 5.11-4.98 (m, 4 H); 4.00 (q, J=6.6 Hz, 2 H); 3.84 (s, 3 H); 2.61 (t, J=7.8 Hz, 2 H); 2.36 (s, 3 H); 2.17 (s, 3 H); 1.93-1.85 (m, 2 H).

Step G: Methyl 5-(3-{[bis(benzyloxy)phosphoryl]oxy}propyl)-2-hydroxy-3-methylbenzoate $K_2CO_3$ (108 mg, 0.784 mmol) was added to a stirred solution of methyl 2-(acetyloxy)-5-(3-{[bis(benzyloxy)phosphoryl]oxy}propyl)-3-methylbenzoate (206.3 mg, 0.392 mmol) in MeOH (26.1 mL) at 25° C. The reaction was stirred at 25° C. for 1 h. The reaction mixture was concentrated in vacuo and the resulting residue was partitioned between water (20 mL) and EtOAc (20 mL). The aqueous layer was separated and extracted with EtOAc (2×20 mL). The combined organic extracts were dried ($MgSO_4$) and concentrated in vacuo to afford methyl 5-(3-{[bis(benzyloxy)phosphoryl]oxy}propyl)-2-hydroxy-3-methylbenzoate, as a colorless oil. LCMS calc.=485.2; found=485.0 (M+H)$^+$.

INTERMEDIATE 11

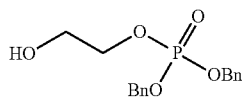

Dibenzyl 2-hydroxyethyl phosphate

To a stirred solution of 2-bromoethanol (200 mg, 1.600 mmol) in anhydrous toluene (15 mL) was added silver dibenzylphosphate (616 mg, 1.600 mmol) and the resultant mixture was heated at reflux for 4 h. The reaction mixture was filtered through Celite, and washed through with additional toluene (2×25 mL). The combined organic extracts were concentrated in vacuo and the resulting crude product purified by flash chromatography (75% EtOAc/hexanes) to afford dibenzyl 2-hydroxyethyl phosphate, as a colorless oil.

INTERMEDIATE 12

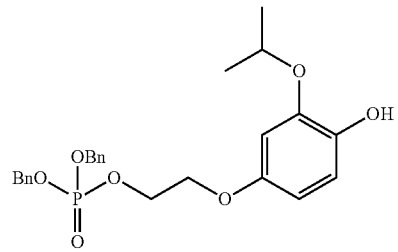

Dibenzyl 2-(4-hydroxy-3-isopropoxyphenoxy)ethyl phosphate

Step A: 4-(Benzyloxy)-2-isopropoxybenzaldehyde $K_2CO_3$ (9.62 g, 69.6 mmol) and 2-iodopropane (2.00 mL, 20.00 mmol) were added successively to a stirred solution of 4-benzyloxy-2-hydroxybenzaldehyde (3.65 g, 16.0 mmol) in dry DMF (20.0 mL) at 25° C. under $N_2$. The reaction was heated at 50° C. overnight. The reaction was diluted with water (50 mL) and extracted with $Et_2O$ (3×50 mL). The combined extracts were dried ($MgSO_4$) and concentrated in vacuo to afford 4-(benzyloxy)-2-isopropoxybenzaldehyde. LCMS calc.=293.1; found=292.9 (M+Na)$^+$.

Step B: 4-Hydroxy-2-isopropoxybenzaldehyde

A suspension of 10% palladium on carbon (0.793 g, 0.745 mmol) in a solution of 4-(benzyloxy)-2-isopropoxybenzaldehyde (4.03 g, 14.91 mmol) and 1-methyl-1,4-cyclohexadiene (16.75 mL, 149 mmol) in DOH (298 mL) was heated at reflux for 2 h. The reaction mixture was cooled to room temperature, filtered through a plug of Celite and washed through with EtOAc. The filtrate was concentrated in vacuo to afford 4-hydroxy-2-isopropoxybenzaldehyde, as a colorless solid. LCMS calc.=181.1; found=181.0 (M+H)$^+$. $^1$H NMR (500 MHz, $CHCl_3$): δ 10.12 (s, 1H); 7.74 (d, J=8.6 Hz, 1 H); 6.52 (dd, J=8.7, 2.1 Hz, 1 H); 6.47 (d, J=2.1 Hz, 1 H); 4.62-4.54 (m, 1 H); 1.36 (d, J=6.1 Hz, 6 H).

4-Hydroxy-2-isopropoxybenzaldehyde was used to synthesize dibenzyl 2-(4-hydroxy-3-isopropoxyphenoxy)ethyl phosphate using methods analogous to those described in INTERMEDIATE 9 and 10 above.

INTERMEDIATE 13

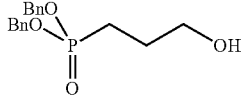

Dibenzyl (3-hydroxypropyl)phosphonate

Step A: Dibenzyl [3-(tetrahydro-2H-pyran-2-yloxy)propyl]phosphonate

Dibenzyl phosphite (1.70 mL, 7.63 mmol) was added to a stirred suspension of sodium hydride (60% dispersion in mineral oil) (0.381 g, 9.53 mmol) in dry DMF (11.4 mL) at 25° C. under $N_2$. After 15 min 2-(3-bromopropoxy)tetrahydro-2H-pyran (1.29 mL, 7.63 mmol) was added and the mixture was stirred at 25° C. for 5 h. The reaction mixture was diluted with water (20 mL) and extracted with Et$_2$O (2×40 mL). The combined organic extracts were washed with brine (20 mL), dried (Na$_2$SO$_4$) and concentrated in vacuo to afford dibenzyl [3-(tetrahydro-2H-pyran-2-yloxy)propyl]phosphonate. R$_f$=0.06 (20% EtOAc/hexanes). LCMS calc.=427.17; found=427.15 (M+Na)$^+$.

Step B: Dibenzyl (3-hydroxypropyl)phosphonate

A solution of dibenzyl [3-(tetrahydro-2H-pyran-2-yloxy) propyl]phosphonate (3.08 g, 7.62 mmol) and pyridinium p-toluenesulfonate (0.191 g, 0.762 mmol) in EtOH (76 mL) was stirred at 55° C. overnight. The reaction mixture was cooled to room temperature and concentrated in vacuo to give the crude product. This was purified by flash chromatography (Biotage Horizon, 40M, Si, ~30 mL/min, 100% hexanes for 360 mL, gradient to 100% EtOAc in hexanes over 3096 mL, 100% EtOAc for 3888 mL) to afford dibenzyl (3-hydroxypropyl)phosphonate. R$_f$=0.34 (EtOAc). LCMS calc.=321.13; found=321.04 (M+H)$^+$. $^1$H NMR (500 MHz, CHCl$_3$): δ 7.35-7.28 (m, 10 H); 5.02 (dd, J=11.9, 8.9 Hz, 2 H); 4.94 (dd, J=11.9, 8.0 Hz, 2 H); 3.60 (t, J=5.6 Hz, 2 H); 3.37 (s, 1 H); 1.90-1.75 (m, 4 H).

INTERMEDIATE 14

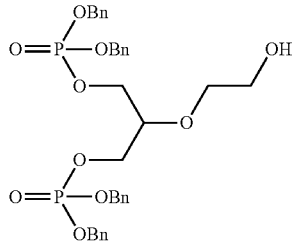

Tetrabenzyl 2-(2-hydroxyethoxy)propane-1,3-diylbis(phosphate)

Step A: 2-Phenyl-5-[2-(tetrahydro-2H-pyran-2-yloxy)ethoxy]-1,3-dioxane

Sodium hydride (60% disp. in mineral oil) (0.666 g, 16.65 mmol) was added to a stirred solution of 1,3-benzylidene glycerol (1.00 g, 5.55 mmol) in dry DMF (13.9 mL). The reaction mixture was stirred at room temperature for 1 h. 2-(2-bromoethoxy)tetrahydro-2H-pyran (1.26 mL, 8.32 mmol) was added dropwise and the reaction mixture was stirred at room temperature overnight. The reaction was diluted with CH$_2$Cl$_2$ (50 mL) and washed with water (50 mL). The aqueous layer was washed with CH$_2$Cl$_2$ (25 mL). The combined organic layers were washed with brine (50 mL), dried (MgSO$_4$) and concentrated in vacuo to give the crude product. This was purified by flash chromatography (Biotage Horizon, 40M, Si, ~30 mL/min, 100% hexanes for 360 mL, gradient to 50% EtOAc in hexanes over 4536 mL) to afford 2-phenyl-5-[2-(tetrahydro-2H-pyran-2-yloxy)ethoxy]-1,3-dioxane, as a colorless oil. R$_f$0.54 (50% EtOAc/hexanes). LCMS calc.=309.17; found=309.05 (M+H)$^+$.

Step B: 2-(2-(Tetrahydro-2H-pyran-2-yloxy)ethoxyl-propane-1,3-diol

A suspension of 10% palladium on carbon (172 mg, 0.162 mmol) in a solution of 2-phenyl-5[2-(tetrahydro-2H-pyran-2-yloxy)ethoxy]-1,3-dioxane (498.9 mg, 1.618 mmol) in EtOAc (32.4 mL) was stirred under H$_2$ at 25° C. for 3 days. The reaction mixture was filtered through a plug of Celite and the filtrate was concentrated in vacuo to afford 2-[2-(tetrahydro-2H-pyran-2-yloxy)ethoxy]propane-1,3-diol. LCMS calc.=243.12; found=243.22 (M+Na)$^+$.

Step C: Tetrabenzyl 2-[2-(tetrahydro-2H-pyran-2-yloxy)ethoxy]propane-1,3-diylbis(phosphate)

Dibenzyl N,N-diisopropylphosphoramidite (1.43 mL, 4.26 mmol) was added to a stirred solution of 1H-tetrazole (0.45 M in CH$_3$CN) (18.9 mL, 8.52 mmol) and 2-[2-(tetrahydro-2H-pyran-2-yloxy)ethoxy]propane-1,3-diol (312.6 mg, 1.419 mmol) in dry CH$_2$Cl$_2$ (17.0 mL) at 25° C. under N$_2$. The reaction was stirred for 2 h at 25° C. The reaction mixture was cooled to 0° C. and a solution of 3-chloroperoxybenzoic acid (1272 mg, 5.68 mmol) in dry CH$_2$Cl$_2$ (11.4 mL) was added via cannula and the reaction was stirred at 0° C. After 60 min the reaction was diluted with EtOAc (50 mL) and washed with successive portions of saturated Na$_2$SO$_3$ (50 mL) and saturated NaHCO$_3$ (50 mL), dried (Na$_2$SO$_4$) and concentrated in vacuo to afford the crude product. This was purified by flash chromatography (Biotage Horizon, 40M, Si, ~30 mL/min, 100% hexanes for 360 mL, gradient to 100% EtOAc over 4536 mL) to afford tetrabenzyl 2-[2-(tetrahydro-2H-pyran-2-yloxy)ethoxy]propane-1,3-diyibis(phosphate), as a colorless oil. R$_f$=0.64 (EtOAc). LCMS calc.=763.24; found=763.21 (M+Na)$^+$. $^1$H NMR (500 MHz, CHCl$_3$): δ 7.39-7.27 (m, 20 H); 5.11-4.94 (m, 8 H); 4.52 (br s, 1 H); 4.14-3.95 (m, 4 H); 3.80-3.59 (m, 5 H); 3.51-3.34 (m, 2 H); 1.76-1.59 (in, 2 H); 1.52-1.47 (m, 2 H); 1.45 (br s, 2 H).

Step D: Tetrabenzyl 2-(2-hydroxyethoxy)propane-1,3-diylbis(phosphate)

A solution of tetrabenzyl 2-[2-(tetrahydro-2H-pyran-2-yloxy)ethoxy]propane-1,3-diylbis(phosphate) (84.3 mg, 0.114 mmol) and pyridinium p-toluenesulfonate (2.86 mg, 0.011 mmol) in EtOH (1.14 mL) was stirred at 55° C. for 4 h. The reaction mixture was cooled to room temperature and diluted with EtOAc (25 mL), washed with saturated NaHCO$_3$ (10 mL), dried (Na$_2$SO$_4$) and concentrated in vacuo to afford tetrabenzyl 2-(2-hydroxyethoxy)propane-1,3-diyl bis(phosphate). LCMS calc.=657.20; found=657.06 (M+H)$^+$. $^1$H NMR (500 MHz, CHCl$_3$): δ 7.40-7.28 (m, 20 H); 5.10-4.95 (m, 8 H); 4.14-4.04 (m, 2 H); 4.03-3.92 (m, 2 H); 3.76-3.67 (m, 1 H); 3.67-3.56 (m, 2 H); 3.57-3.44 (m, 2 H).

INTERMEDIATE 15

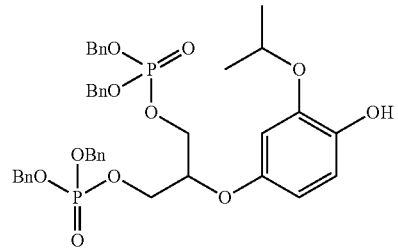

Tetrabenzyl 2-(4-hydroxy-3-isopropoxyphenoxy) propane-1,3-diylbis(phosphate)

Step A: 4-(Benzyloxy)-2-isopropoxybenzaldehyde

K$_2$CO$_3$ (6.14 g, 44.4 mmol) and 2-iodopropane (1.28 mL, 12.76 mmol) were added successively to a stirred solution of 4-benzyloxy-2-hydroxybenzaldehyde (2.33 g, 10.21 mmol) in dry DMF (12.8 mL) at 25° C. under $N_2$. The reaction was heated at 50° C. overnight. The reaction was diluted with water (50 mL) and extracted with $Et_2O$ (3×50 mL). The combined extracts were dried ($MgSO_4$) and concentrated in vacuo to afford the crude product. This was azeotroped from toluene to afford 4-(benzyloxy)-2-isopropoxybenzaldehyde. LCMS calc.=293.1; found=292.9 $(M+Na)^+$.

Step B: 4-(Benzyloxy)-2-isopropoxyphenol

A solution of 4-(benzyloxy)-2-isopropoxybenzaldehyde (2.76 g, 10.21 mmol) and 30 wt % hydrogen peroxide (1.35 mL, 13.07 mmol) in conc. $H_2SO_4$ (0.204 mL) and MeOH (20.4 mL) was stirred for 3 h at 25° C. under $N_2$. After this time the mixture was diluted with water (20 mL) and extracted with $CH_2Cl_2$ (3×30 mL). The combined extracts were dried ($MgSO_4$) and concentrated in vacuo to afford 4-(benzyloxy)-2-isopropoxyphenol, as a colorless oil. LCMS calc.=281.1; found=281.0 $(M+Na)^+$.

Step C: 4-(Benzyloxy)-2-isopropoxyphenyl benzoate

Triethylamine (4.27 mL, 30.7 mmol) was added to a solution of 4-(benzyloxy)-2-isopropoxyphenol (2.64 g, 10.22 mmol) in dry $CH_2Cl_2$ (40.9 mL) and the resulting solution was cooled to 0° C. Benzoyl chloride (1.54 mL, 13.29 mmol) was added dropwise and the reaction was stirred at 25° C. overnight. The reaction mixture was washed with water (50 mL). The aqueous layer was separated and extracted with $CH_2Cl_2$ (2×20 mL). The combined organic layers were dried ($MgSO_4$) and concentrated in vacuo to give the crude product. This was azeoptoped with toluene to afford 4-(benzyloxy)-2-isopropoxyphenyl benzoate. LCMS calc.=385.1; found=385.0 $(M+Na)^+$. $^1$H NMR (500 MHz, $CHCl_3$): δ 8.25-8.21 (2 H, m), 7.66-7.60 (1 H, m), 7.52 (2 H, t, J=7.7 Hz), 7.47 (2 H, d, J=7.5 Hz), 7.44-7.39 (2 H, m), 7.39-7.33 (1 H, m), 7.12-7.05 (1 H, m), 6.73-6.68 (1 H, m), 6.60 (1 H, dd, J=8.7, 2.8 Hz), 5.07 (2 H, s), 4.54-4.43 (1 H, m), 1.27 (6 H, t, J=6.1 Hz).

Step D: 4-Hydroxy-2-isopropoxyphenyl benzoate

A suspension of 10% palladium on carbon (0.543 g, 0.510 mmol) in a solution of 4-(benzyloxy)-2-isopropoxyphenyl benzoate (3.70 g, 10.21 mmol) in EtOAc (25 mL) and EtOH (5 mL) was shaken in a Parr shaker under $H_2$ (45 psi) at 25° C. for 3 days. The reaction mixture was filtered through a plug of Celite and the filtrate was concentrated in vacuo to afford the crude product. This was purified by flash chromatography (Biotage Horizon, 40M, Si, ~30 mL/min, 100% hexanes for 360 mL, gradient to 25% EtOAc in hexanes over 4536 mL) to afford 4-hydroxy-2-isopropoxyphenyl benzoate. $R_f$=0.28 (20% EtOAc in hexanes). LCMS calc.=295.10; found=295.07 $(M+Na)^+$. $^1$H NMR (500 MHz, $CHCl_3$): δ 8.22 (d, j=7.8 Hz, 2 H); 7.64 (t, J=7.4 Hz, 1 H); 7.51 (t, J=7.7 Hz, 2 H); 6.94 (d,J=8.6 Hz, 1 H); 6.49 (d, J=2.7 Hz, 1 H); 6.35 (dd, J=8.6, 2.7 Hz, 1 H); 4.39 (p, J=6.1 Hz, 1 H); 1.22 (d, J=6.1 Hz, 6 H).

Step E: 2-Isopropoxy-4-[(2-phenyl-1,3-dioxan-5-yl)oxy]phenyl benzoate

Diethyl azodicarboxylate (173 μL, 1.102 mmol) was added to a stirred solution of 4-hydroxy-2-isopropoxyphenyl benzoate (200 mg, 0.734 mmol), 1,3-benzylidene glycerol (159 mg, 0.881 mmol) and triphenylphosphine (289 mg, 1.102 mmol) in dry THF (7.34 mL) at room temperature under $N_2$. The reaction was heated at reflux overnight. Another 1.5 eq of $Ph_3P$ and DEAD were added and the reaction was heated at reflux for another 5 h. The reaction mixture was concentrated in vacuo to afford the crude product. This was purified by flash chromatography (Biotage Horizon, 25M, Si, ~20 mL/min, 100% hexanes for 144 mL, gradient to 25% EtOAc in hexanes over 2394 mL) to afford 2-isopropoxy-4-[(2-phenyl-1,3-dioxan-5-yl)oxy]phenyl benzoate, as a colorless solid. $R_f$=0.67 (20% EtOAc in hexanes). LCMS calc.=435.18; found=435.18 $(M+H)^+$. $^1$H NMR (500 MHz, $CHCl_3$): δ 8.26 (d, J=7.8 Hz, 2 H); 7.66 7.5 Hz, 1 H); 7.60-7.51 (m, 4 H); 7.47-7.39 (m, 3 H); 7.12 (d, J=8.7 Hz, 1 H); 6.68 (d, J=2.8 Hz, 1 H); 6.63 (dd, J-8.7, 2.7 Hz, 1 H); 5.56 (s, 1 H); 4.68-4.57 (m, 3 H); 4.53 (p, J=6.1 Hz, 1 H); 3.87 (t, J=9.8 Hz, 2 H); 1.31 (d, J=6.1 Hz, 6 H).

Step F: 4-[2-Hydroxy-1-(hydroxymethypethoxy]-2-isopropoxyphenyl benzoate

A suspension of 10% palladium on carbon (38.9 mg, 0.037 mmol) in a solution of 2-isopropoxy-4-[(2-phenyl-1,3-dioxan-5-yl)oxy]phenyl benzoate (158.7 mg, 0.365 mmol) in EtOAc (3.65 mL) was stirred under $H_2$ (double balloon pressure) at 25° C. for 4 days. The reaction mixture was filtered through a plug of Celite and the filtrate was concentrated in vacuo to afford the crude product. This was purified by flash chromatography (Biotage Horizon, 25M, Si, ~20 mL/min, 100% hexanes for 144 mL, gradient to 100% EtOAc over 2394 mL) to afford 4-[2-hydroxy-1-(hydroxymethyl)ethoxy]-2-isopropoxyphenyl benzoate, as a colorless solid. $R_f$=0.17 (50% EtOAc in hexanes). LCMS calc.=347.15; found=347.06 $(M+H)^+$. $^1$H NMR (500 MHz, $CHCl_3$): δ 8.18 (d, J=7.8 Hz, 2 H); 7.61 (t, J=7.5 Hz, 1 H); 7.49 (t, J=7.7 Hz, 2 H); 7.03 (d, J=8.7 Hz, 1 H); 6.68 (d, J=2.7 Hz, 1 H); 6.56 (dd, J=8.8, 2.7 Hz, 1 H); 4.45 (p, J=6.1 Hz, 1 H); 4.34 (p, J=4.8 Hz, 1 H); 3.89-3.80 (m, 4 H); 2.88 (s, 2 H); 1.23 (d, J=6.1 Hz, 6 H).

Step G: 4-[2-{[Bis(benzyloxy)phosphoryl]oxy}-1-({[bis(benzyloxy)phosphoryl]oxy}methy)ethoxy]-2-isopropoxyphenyl benzoate Dibenzyl N,N-diisopropylphosphoramidite (258 μL, 0.769 mmol) was added to a stirred solution of 1H-tetrazole (0.45 M in $CH_3CN$) (3418 μL, 1.538 mmol) and 4-[2-hydroxy-1-(hydroxymethyl)ethoxy]-2-isopropoxyphenyl benzoate (88.8 mg, 0.256 mmol) in dry $CH_2Cl_2$ (9.50 mL) at 25° C. under $N_2$. The reaction was stirred for 3 h at 25° C. The reaction mixture was cooled to 0° C. and a solution of 3-chloroperoxybenzoic acid (230 μL, 1.025 mmol) in dry $CH_2Cl_2$ (4.75 mL) was added via cannula and the reaction was stirred at 0° C. After 60 min the reaction was diluted with EtOAc (25 mL) and washed with successive portions of saturated $Na_2SO_3$ (20 mL) and saturated $NaHCO_3$ (20 mL), dried ($Na_2SO_4$) and concentrated in vacuo to afford the crude product. This was purified by flash chromatography (Biotage Horizon, 25M, Si, ~20 mL/min, 100% hexanes for 144 mL, gradient to 75% EtOAc in hexanes over 2394 mL) to afford 4-[2-{[bis(benzyloxy)phosphoryl]oxy}-1-({[bis(benzyloxy)phosphoryl]oxy}methyl)ethoxy]-2-isopropoxyphenyl benzoate, as a colorless oil. $R_f$=0.41 (50% EtOAc in hexanes). LCMS calc.=867.27; found=867.14 (M+H)$^+$. $^1$H NMR (500 MHz, CHCl$_3$): δ 8.20 (d, J=7.7 Hz, 2 H); 7.63 (t, J=7.5 Hz, 1 H); 7.51 (t, J=7.7 Hz, 2 H); 7.44-7.20 (m, 20 H); 6.98 (d, J=8.7 Hz, 1 H); 6.61 (d, J=2.8 Hz, 1 H); 6.44 (dd, J=8.7, 2.8 Hz, 1 H); 5.08-4.98 (m, 8 H); 4.44 (p, J=5.0 Hz, 1 H); 4.36 (p, J=6.1 Hz, 1 H); 4.14 (dd, J=7.2, 5.0 Hz, 4 H); 1.18 (d, J=6.1 Hz, 6 H).

Step H: Tetrabenzyl 2-(4-hydroxy-3-isopropoxyphenoxy)propane-1,3-diylbis(phosphate)

0.1% (w/v) NaOH in water/MeOH (1:9) (1737 μL, 0.043 mmol) was added to a stirred solution of 4-[2-{[bis(benzyloxy)phosphoryl]oxy}-1-({[bis(benzyloxy)phosphoryl] oxy}methyl)ethoxy]-2-isopropoxyphenyl benzoate (125.5 mg, 0.145 mmol) in MeOH (4.83 mL) at 25° C. Another 3×0.3 eq 0.1% (w/v) NaOH in water/MeOH were added. After 24 h, the reaction mixture was concentrated in vacuo to remove most of the MeOH. The aqueous mixture was diluted with water (10 mL) and 1N HCl (5 mL) and extracted with EtOAc (3×15 mL). The combined extracts were dried (Na$_2$SO$_4$) and concentrated in vacuo to give the crude product. This was purified by flash chromatography (Biotage Horizon, 25M, Si, ~20 mL/min, 100% hexanes for 144 mL, gradient to 100% EtOAc over 2394 mL) to afford tetrabenzyl 2-(4-hydroxy-3-isopropoxyphenoxy)propane-1,3-diylbis (phosphate), as a colorless oil. $R_f$=0.19 (50% EtOAc in hexanes). LCMS calc.=763.24; found=763.07 (M+H)$^+$. $^1$H NMR (500 MHz, CHCl$_3$): δ 7.31 (m, 20 H); 6.77 (d, J=8.7 Hz, 1 H); 6.54 (d, J=2.7 Hz, 1 H); 6.37 (dd, J=8.7, 2.7 Hz, 1 H); 5.67 (s, 1 H); 5.07-4.98 (m, 8 H); 4.41 (p, J=6.1 Hz, 1 H); 4.34 (p, J=5.00 Hz, 1 H); 4.14 (t, J=6.1 Hz, 4 H); 1.28 (d, J=6.1 Hz, 6 H).

Example 1

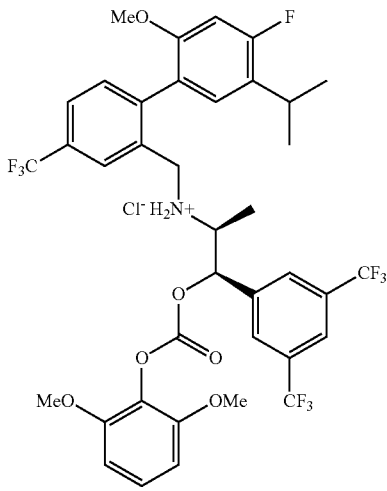

(1R,2S)-1-[3,5-Bis(trifluoromethyl)phenyl]-1-{[2,6-dimethoxyphenoxy)carbonyl]oxy}-N-{[4'-fluoro-5'-isopropyl-2'-methoxy-4-(trifluoromethyl)biphenyl-2-yl]methyl}propan-2-aminium chloride Step A: (1R,2S)-1-[3,5-Bis(trifluoromethyl)phenyl]-2-((tert-butoxycarbonyl){[4'-fluoro-5'-isopropyl-2'-methoxy-4-(trifluoromethyl)biphenyl-2-yl] methyl}amino)propyl 2,6-dimethoxyphenyl carbonate Pyridine (0.035 mL, 0.437 mmol) was added dropwise to a stirred solution of 2,6-dimethoxyphenol (67.4 mg, 0.437 mmol) and triphosgene (47.4 mg, 0.160 mmol) in dry CH$_2$Cl$_2$ (4 mL) at 0° C. under N$_2$. The reaction was stirred at 25° C. for 1.5 h. A solution of tert-butyl {(1S,2R)-2-[3,5-bis(trifluoromethyl)phenyl]-2-hydroxy-1-methylethyl}{[4'-fluoro-5'-isopropyl-2'-methoxy-4-(trifluoromethyl)biphenyl-2-yl] methyl}carbamate (INTERMEDIATE 7, 155.6 mg, 0.219 mmol) in dry CH$_2$Cl$_2$ (2 mL) was added via cannula followed by dropwise addition of pyridine (0.040 mL, 0.492 mmol). The reaction was stirred at 25° C. for 3 h. The reaction was diluted with water (15 mL) and extracted with EtOAc (3×20 mL). The combined extracts were dried (MgSO$_4$) and concentrated in vacuo to give the crude product. This was purified by flash chromatography (Biotage Horizon, 25M, Si, ~20 mL/min, 100% hexanes for 144 mL, gradient to 20% EtOAc in hexanes over 2394 mL) to give (1R,2S)-1-[3,5-bis(trifluoromethyl)phenyl]-2-((tert-butoxycarbonyl){[4'-fluoro-5'-isopropyl-2!-methoxy-4-(trifluoromethyl)biphenyl-2-yl] methyl}amino)propyl 2,6-dimethoxyphenyl carbonate, as a colorless oil. $R_f$=0.51 (20% EtOAc/hexanes). LCMS calc.=914.3; found=914.1 (M+H)$^+$.

Step B: (1R,2S)-1-[3,5-Bis(trifluoromethyl)phenyl]-1-{[(2,6-dimethoxyphenoxy)carbonyl]oxy}-N-{[4'-fluoro-5'-isopropyl-2'-methoxy-4-(trifluoromethyl) biphenyl-2-yl]methyl}propan-2-aminium chloride A solution of (1R,2S)-1-[3,5-bis(trifluoromethyl)phenyl]-2-((tert-butoxycarbonyl){[4'-fluoro-5'-isopropyl-2'-methoxy-4-(trifluoromethyl)biphenyl-2-yl]methyl}amino)propyl 2,6-dimethoxyphenyl carbonate (125.7 mg, 0.141 mmol) in HCl saturated EtOAc (4 mL) was stirred at 25° C. for 5 h. The reaction mixture was concentrated in vacuo to afford (1R,2S)-1-[3,5-bis(trifluoromethyl)phenyl]-1-{[(2,6-dimethoxyphenoxy)carbonyl]oxy}-N-{[4'-fluoro-5'-isopropyl-2'-methoxy-4-(trifluoromethyl)biphenyl-2-yl]methyl}propan-2-aminium chloride, as a colorless oil/glass. LCMS calc.=792.2; found=792.2 (M+H)$^+$.

The following carbonates (Table 2) were synthesized using methods analogous to those described in EXAMPLE 1 from commercially available choloroformates, chlorothioformates, phenols and alcohols. The conditions employed in EXAMPLE 1, Step B were also successful in removing any text-butyl carbamate or ester groups present in the alcohol or phenol residue of the carbamate such as that present in INTERMEDATE 5.

TABLE 2

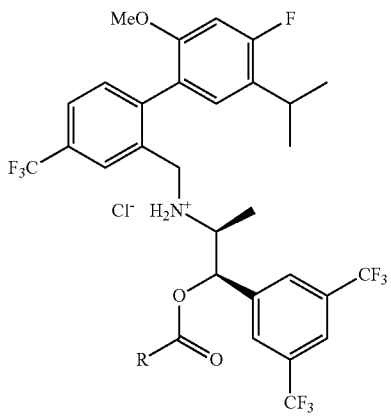

| Example | R | LCMS (M + H)+ |
|---|---|---|
| 2 | methoxymethyl | 669.8 |
| 3 | ethoxymethyl | 683.9 |
| 4 | ethoxycarbonylmethoxy | 742.0 |
| 5 | benzyloxycarbonylmethoxy | 804.1 |
| 6 | ethoxycarbonyl(phenyl)methoxy | 818.1 |
| 7 | diethyl malonate-2-oxy | 814.0 |
| 8 | (S)-dimethyl succinate-2-oxy | 799.9 |
| 9 | methylthio | 686.0 |

TABLE 2-continued

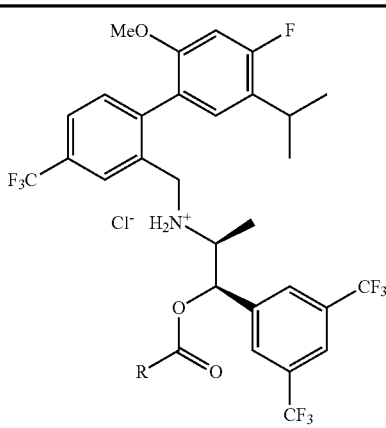

| Example | R | LCMS (M + H)+ |
|---|---|---|
| 10 | ethylthio | 700.0 |
| 11 | benzyloxy | 746.0 |
| 12 | 4-(methoxycarbonyl)benzyloxy | 804.0 |
| 13 | 4-methoxyphenoxy | 761.9 |
| 14 | 2,3,4-trimethoxyphenoxy | 822.0 |
| 15 | 2,4-dimethoxyphenoxy | 792.0 |
| 16 | 2,3,4-trimethoxyphenoxy | 822.0 |

TABLE 2-continued
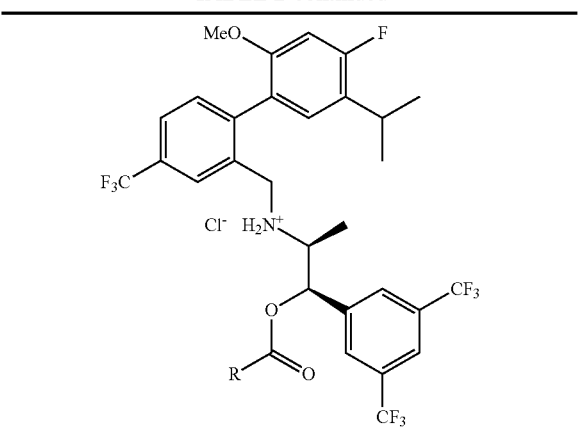
| Example | R | LCMS (M + H)+ |
|---|---|---|
| 17 | 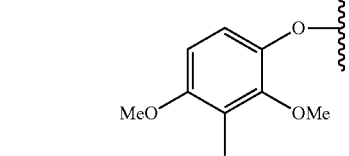 | 806.1 |
| 18 | 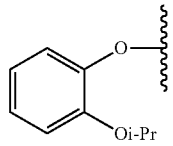 | 790.1 |
| 19 | 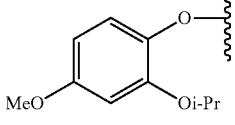 | 820.0 |
| 20 | 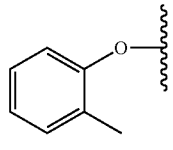 [SMILES: *Oc1ccccc1C] | 746.7 |
| 21 | 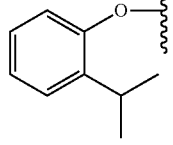 | 774.1 |
| 22 | 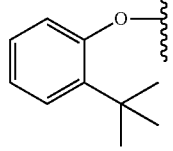 | 788.1 |
| 23 | 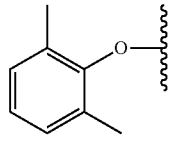 [SMILES: *Oc1c(C)cccc1C] | 760.1 |
TABLE 2-continued
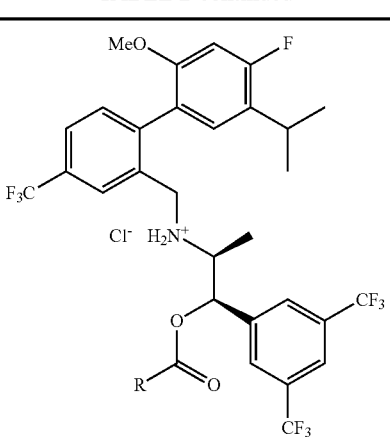
| Example | R | LCMS (M + H)+ |
|---|---|---|
| 24 | 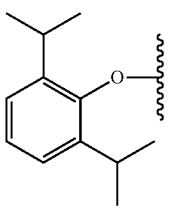 [SMILES: *Oc1c(C(C)C)cccc1C(C)C] | 816.1 |
| 25 | 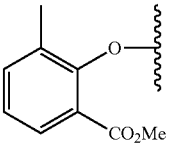 | 804.2 |
| 26 | 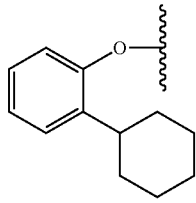 [SMILES: *Oc1ccccc1C1CCCCC1] | 814.2 |
| 27 | 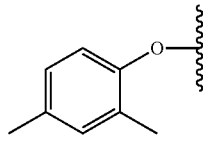 [SMILES: *Oc1ccc(C)cc1C] | 760.1 |
| 28 | 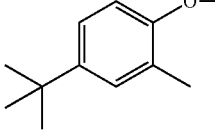 | 802.6 |
| 29 | 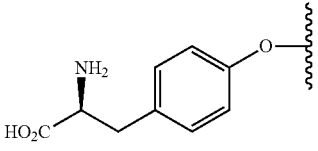 | 818.9 |

TABLE 2-continued

| Example | R | LCMS (M + H)+ |
|---|---|---|
| 30 | (structure: NH2, MeO2C, phenyl-O-) | 833.1 |
| 31 | (structure: NH2, HO2C, phenyl(OMe)-O-) | 848.9 |

Example 32

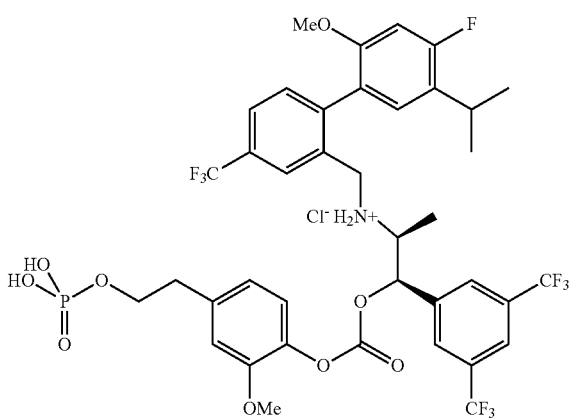

(1R,2S)-1-[3,5-Bis(trifluoromethyl)phenyl]-N-{[4'-fluoro-5'-isopropyl-2'-methoxy-4-(trifluoromethyl)biphenyl-2-yl]methyl}-1-[({2-methoxy-4-[2-(phosphonooxy)ethyl]phenoxy}carbonyl)oxy]propan-2-aminium chloride Step A: 4-(2-Hydroxyethyl)-2-methoxyphenyl acetate A solution of 1-acetyl-1H-1,2,3-triazolo[4,5-b]pyridine (0.964 g, 5.95 mmol) in dry THF (24 mL) was added to a solution of homovanillyl alcohol (1.00 g, 5.95 mmol) in 1N aq. NaOH (5.95 mL, 5.95 mmol) at 25° C. The reaction was stirred at 25° C. for 60 min. The reaction was diluted with 1N HCl (40 mL) and extracted with Et$_2$O (3×50 mL). The combined extracts were dried (MgSO$_4$) and concentrated in vacuo to give the crude product. This was purified by flash chromatography (Biotage Horizon, 40M, Si, ~30 mL/min, 100% hexanes for 144 mL, gradient to 50% EtOAc in hexanes over 360 mL, gradient to 100% EtOAc over 1944 mL) to afford 4-(2-hydroxyethyl)-2-methoxyphenyl acetate, as a colorless oil. R$_f$=0.71 (EtOAc). LCMS calc.=233.1; found=233.1 (M+Na)$^+$. $^1$H NMR (500 MHz, CDCl$_3$): δ 6.95 (d, J=8.0 Hz, 1 H); 6.83 (d, J=1.8 Hz, 1 H); 6.79 (dd, J=1.8, 8.0 Hz, 1 H); 3.88 (t, J=6.6 Hz, 2 H), 3.84 (s, 3 H); 2.82 (t, J=6.5 Hz, 2 H); 2.30 (s, 3 H); 1.76 (s, 1 H).

Step B: 2-Methoxy-4-(2-{[(4-methylphenyl)sulfonyl]oxy}ethyl)phenyl acetate p-Toluenesulfonyl chloride (2.14 mL, 11.2 mmol) was added to a stirred solution of 4-(2-hydroxyethyl)-2-methoxyphenyl acetate (1.18 g, 5.61 mmol) in dry pyridine (20 mL) at 0° C. under N$_2$. The reaction was stored at 4° C. for 3 days. The reaction was diluted with water (50 mL) and extracted with EtOAc (3×50 mL). The combined extracts were dried (MgSO$_4$) and concentrated in vacuo to afford 2-methoxy-4-(2-{[(4-methylphenyl)sulfonyl]oxy}ethyl)phenyl acetate, as an oil. Product was a 6:4 mixture of desired product and starting material but carried forward regardless. LCMS calc.=387.1; found=386.8 (M+Na)$^+$.

Step C: 4-(2-Iodoethyl)-2-methoxyphenyl acetate

A 6:4 mixture of 2-methoxy-4-(2-{[(4-methylphenyl)sulfonyl]oxy}ethyl)phenyl acetate and 4-(2-hydroxyethyl)-2-methoxyphenyl acetate (1.57 g, 4.31 mmol) and sodium iodide (0.706 mL, 17.2 mmol) in dry acetone (28 mL) was stirred at room temperature overnight with protection from light. The acetone was removed in vacuo and the residue was triturated with toluene and filtered through a plug of Celite to remove insoluble inorganic material. The filtrate was concentrated in vacuo to afford the crude product. This was purified by flash chromatography (Biotage Horizon, 40M, Si, ~30 mL/min, 100% hexanes for 360 mL, gradient to 50% EtOAc in hexanes over 4536 mL) to give 4-(2-iodoethyl)-2-methoxyphenyl acetate. R$_f$=0.58 (20% EtOAc/hexanes). LCMS calc.=321.0; found=320.7 (M+H)$^+$.

Step D: 4-(2-{[Bis(benzyloxy)phosphoryl]oxy}ethyl)-2-methoxyphenyl acetate

Silver dibenzylphosphate (0.950 g, 2.47 mmol) was added to a solution of 4-(2-iodoethyl)-2-methoxyphenyl acetate (0.79 g, 2.47 mmol) in dry toluene (20 mL) and the mixture was heated at reflux overnight. The precipitated formed was removed by filtration through a plug of Celite and washed through with toluene. The filtrate was concentrated in vacuo to give the crude product. This was purified by flash chromatography (Biotage Horizon, 40M, Si, ~30 mL/min, 100% hexanes for 360 mL, gradient to 50% EtOAc in hexanes over 4536 mL) to afford 4-(2-{[bis(benzyloxy)phosphoryl]oxy}ethyl)-2-methoxyphenyl acetate, as a colorless oil. R$_f$=0.31 (%0% EtOAc/hexanes). LCMS calc.=471.2; found=470.9 (M+Na)$^+$. $^1$H NMR (600 MHz, CDCl$_3$): δ 7.37-7.31 (m, 10 H); 6.92 (d, J=8.0 Hz, 1 H); 6.76 (d, J=1.8 Hz, 1

H); 6.72 (dd, J=1.9, 8.0 Hz, 1 H); 5.01-4.95 (m, 4 H); 4.17 (q, J=7.2 Hz, 2 H); 3.76 (s, 3 H); 2.89 (t, J=7.0 Hz, 2 H); 2.30 (s, 3 H).

Step E: Dibenzyl 2-(4-hydroxy-3-methoxyphenyl)ethyl phosphate $K_2CO_3$ (126 mg, 0.910 mmol) was added to a stirred solution of 4-(2-{[bis(benzyloxy)phosphoryl]oxy}ethyl)-2-methoxyphenyl acetate (214 mg, 0.455 mmol) in MeOH (30 mL) at 25° C. The reaction was stirred at 25° C. for 1 h. The reaction mixture was concentrated in vacuo and the resulting residue was partitioned between water (20 mL) and EtOAc (20 mL). The aqueous layer was separated and extracted with EtOAc (2×20 mL). The combined organic extracts were dried ($MgSO_4$) and concentrated in vacuo to afford dibenzyl 2-(4-hydroxy-3-methoxyphenyl)ethyl phosphate, as an oil. LCMS calc.=429.2; found=429.1 (M±Na)$^+$.

Step F: 4-(2-{[Bis(benzyloxy)phosphoryl] oxy}ethyl)-2-methoxyphenyl (1R,2S)-1-[3,5-bis(trifluoromethyl)phenyl]-2-((tert-butoxycarbonyl){[4'-fluoro-5'-isopropyl-2'-methoxy-4-(trifluoromethyl) biphenyl-2-yl]methyl}amino)propyl carbonate Pyridine (0.037 mL, 0.455 mmol) was added dropwise to a stirred solution of dibenzyl 2-(4-hydroxy-3-methoxyphenyl) ethyl phosphate (195 mg, 0.455 mmol) and triphosgene (49.3 mg, 0.166 mmol) in dry $CH_2Cl_2$ (4 mL) at 0° C. under $N_2$. The reaction was stirred at 25° C. for 1.5 h. A solution of tert-butyl {(1S,2R)-2-[3,5-bis(trifluoromethyl)phenyl]-2-hydroxy-1-methylethyl}{[4'-fluoro-5'-isopropyl-2'-methoxy-4-(trifluoromethyl)biphenyl-2-yl]methyl}carbamate (INTERMEDIATE 7, 162.0 mg, 0.228 mmol) in dry $CH_2Cl_2$ (2 mL) was added via cannula followed by dropwise addition of pyridine (0.041 mL, 0.512 mmol). The reaction was stirred at 25° C. for 3 h. The reaction was diluted with water (15 mL) and extracted with EtOAc (3×20 mL). The combined extracts were dried ($MgSO_4$) and concentrated in vacuo to give the crude product. This was purified by flash chromatography (Biotage Horizon, 25M, Si, ~20 mL/min, 100% hexanes for 144 mL, gradient to 50% EtOAc in hexanes over 2394 mL) to give 4-(2-{[bis(benzyloxy)phosphoryl]oxy}ethyl)-2-methoxyphenyl (1R,2S)-1-[3,5-bis(trifluoromethyl)phenyl]-2-((tert-butoxycarbonyl){[4'-fluoro-5'-propyl-2'-methoxy-4-(trifluoromethyl)biphenyl-2-yl]methyl}amino)propyl carbonate, as a colorless oil. $R_f$=0.63 (50% EtOAc/hexanes). LCMS calc.=1166.4; found=1166.4 (M+H)$^+$.

Step G: (1R,2S)-1-[3,5-Bis(trifluoromethyl)phenyl]-2-((tert-butoxycarbonyl){[4'-fluoro-5'-isopropyl-2'-methoxy-4-(trifluoromethyl)biphenyl-2-yl]methyl}amino)propyl 2-methoxy-4-[2-(phosphonooxy)ethyl]phenyl carbonate A suspension of 10% palladium on carbon (7.9 mg, 0.074 mmol) in a solution of 4-(2-{[bis(benzyloxy)phosphoryl] oxy}ethyl)-2-methoxyphenyl (1R,2S)-1-[3,5-bis(trifluoromethyl)phenyl]-2-((tert-butoxycarbonyl){[4'-fluoro-5'-isopropyl-2'-methoxy-4-(trifluoromethyl)biphenyl-2-yl] methyl}amino)propyl carbonate (86.2 mg, 0.074 mmol) in ethanol (5.7 mL) was stirred under $H_2$ (double balloon pressure) at 25° C. for 5 h. The reaction mixture was filtered through a plug of Celite and the filtrate was concentrated in vacuo to afford (1R,2S)-1-[3,5-bis(trifluoromethyl)phenyl]-2-((tert-butoxycarbonyl){[4'-fluoro-5'-isopropyl-2'-methoxy-4-(trifluoromethyl)biphenyl-2-yl]methyl}amino)propyl 2-methoxy-4-[2-(phosphonooxy)ethyl]phenyl carbonate. LCMS calc.=1008.8; found=1008.8 (M+Na)$^+$.

Step H: (1R,2S)-1-[3,5-Bis(trifluoromethyl)phenyl]-N-{[4'-fluoro-5'-isopropyl-2'-methoxy-4-(trifluoromethyl)biphenyl-2-yl]methyl}-1-[({2-methoxy-4-[2-(phosphonooxy)ethyl]phenoxy}carbonyl)oxy] propan-2-aminium chloride A solution of (1R,2S)-1-[3,5-bis(trifluoromethyl)phenyl]-2-((tert-butoxycarbonyl){[4'-fluoro-5'-isopropyl-2'-methoxy-4-(trifluoromethyl)biphenyl-2-yl]methyl}amino)propyl 2-methoxy-4-[2-(phosphonooxy)ethyl]phenyl carbonate (72.9 mg, 0.074 mmol) in HCl saturated EtOAc (2 mL) was stirred at 25° C. for 5 h. The reaction mixture was concentrated in vacuo to afford (1R,2S)-1-[3,5-bis(trifluoromethyl) phenyl]-N-{[4'-fluoro-5'-isopropyl-2'-methoxy-4-(trifluoromethyl)biphenyl-2-yl]methyl}-1-[({2-methoxy-4-[2-(phosphonooxy)ethyl]phenoxy}carbonyl)oxy]propan-2-aminium chloride, as a colorless oil/glass. LCMS calc.=886.2; found=886.0 (M+H)$^+$.

The following carbonates (Table 3) were synthesized using methods analogous to those described in EXAMPLE 32 from commercially available alcohols or those whose syntheses are described above.

TABLE 3

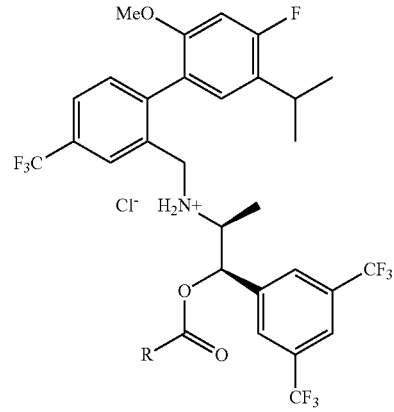

| Example | R | LCMS (M + H)$^+$ |
|---|---|---|
| 33 | 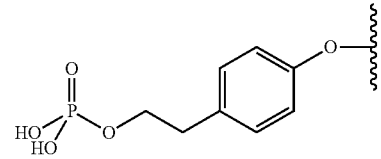 [SMILES: *Oc1ccc(CCOP(=O)(O)O)cc1] | 855.9 |
| 34 |  | 772.31 |

TABLE 3-continued
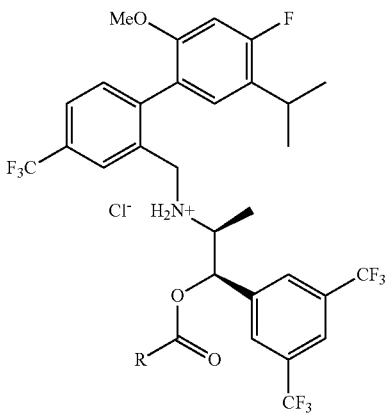
| Example | R | LCMS (M + H)+ |
|---|---|---|
| 35 | (HOOC-CH2-CH(COOH)-O~) | 772.17 |
| 36 | (HOOC-CH2-CH(COOH)-O~) | 772.06 |
| 37 | HO-P(O)(OH)-CH2CH2CH2-O~ | 778.05 |
| 38 | (HO)2P(O)-O-CH2-CH(O-CH2CH2-O~)-CH2-O-P(O)(OH)2 | 934.25 |
| 39 | 4-(2-(phosphonooxy)ethoxy)-2-methoxyphenyl-O~ | 902.0 |
TABLE 3-continued
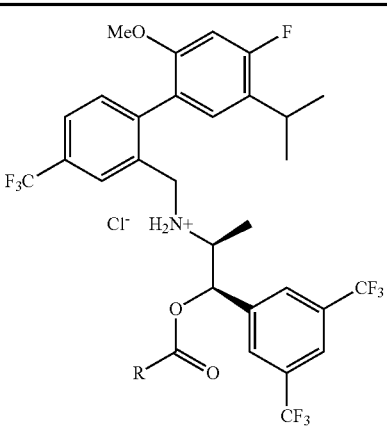
| Example | R | LCMS (M + H)+ |
|---|---|---|
| 40 | 2-(MeO2C)-6-methyl-4-(3-(phosphonooxy)propyl)phenyl-O~ | 942.1 |
| 41 | (HO)2P(O)-O-CH2CH2-O~ | 780.09 |
| 42 | 4-(2-(phosphonooxy)ethoxy)-2-isopropoxyphenyl-O~ | 930.1 |

TABLE 3-continued

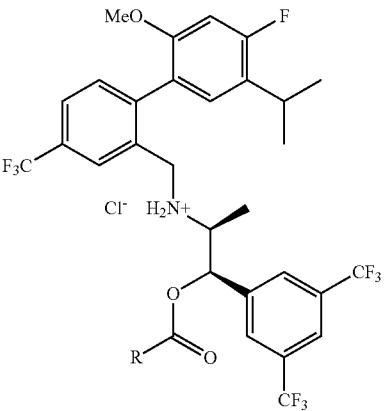

| Example | R | LCMS (M + H)⁺ |
|---|---|---|
| 43 | 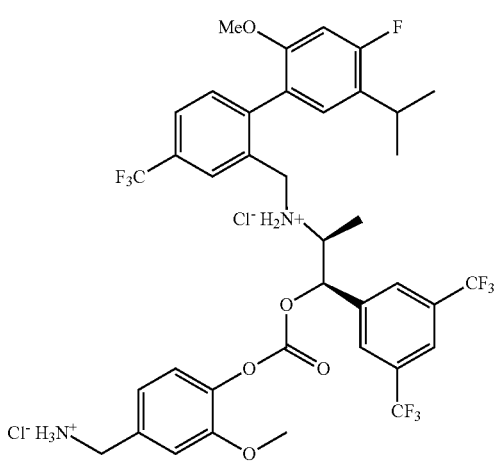 | 1040.23 |

Example 44

(1R,2S)-1-({[4-(Ammoniomethyl)-2-methoxyphenoxy]carbonyl}oxy)-1-[3,5-bis(trifluoromethyl)phenyl]-N-{[4'-fluoro-5'-isopropyl-2'-methoxy-4-(trifluoromethyl)biphenyl-2-yl]methyl}propan-2-aminium dichloride Step A: tert-Butyl(4-hydroxy-3-methoxybenzyl)carbamate To a solution of 4-hydroxy-3-methoxybenzylamine (1.0 g, 5.27 mmol) in acetonitrile (30 mL) was added tert-butyldicarbonate (1.27 g, 5.80 mmol) and di-isopropylethylamine (1.84 mL, 10.54 mmol). The reaction was stirred at room temperature for 16 h before being partitioned between EtOAc (60 mL) and water (30 mL). The aqueous phase was separated and re-extracted with EtOAc (3×25 mL) and the combined organic extracts were washed with brine (60 mL), dried over $MgSO_4$, filtered and concentrated. Purification by flash chromatography (40% EtOAc/hexanes) gave tert-Butyl(4-hydroxy-3-methoxybenzyl)carbamate. LCMS 275.9 (M+1)⁺.

Step B: (1R,2S)-1-[3,5-Bis(trifluoromethyl)phenyl]-2-((tert-butoxycarbonyl){[4'-fluoro-5'-isopropyl-2'-methoxy-4-(trifluoromethyl)biphenyl-2-yl]methyl}amino)propyl-4-{[tert-butoxycarbonyl)amino]methyl}-2-methoxyphenyl carbonate Pyridine (0.048 mL, 0.587 mmol) was added dropwise to a stirred solution of tert-butyl(4-hydroxy-3-methoxybenzyl)carbamate (149 mg, 0.587 mmol) and triphosgene (64 mg, 0.214 mmol) in dry $CH_2Cl_2$ (4.0 mL) at 0° C. under $N_2$. The reaction was stirred at 25° C. for 1.5 h. A solution of tert-butyl {(1S,2R)-2-[3,5-bis(trifluoromethyl)phenyl]-2-hydroxy-1-methylethyl)}{[4'-fluoro-5'-isopropyl-2'-methoxy-4-(trifluoromethyl)biphenyl-2-yl]methyl}carbamate (INTERMEDIATE 7, 209 mg, 0.294 mmol) in dry $CH_2Cl_2$ (2 mL) was added followed by dropwise addition of pyridine (0.053 mL, 0.587 mmol). The reaction was stirred at 25° C. for 3 h. The reaction was diluted with water (15 mL) and extracted with EtOAc (3×20 mL). The combined extracts were dried ($MgSO_4$) and concentrated in vacuo to give the crude product. This was purified by flash chromatography (0-20% gradient EtOAc/hexanes over 30 min) to give (1R,2S)-1-[3,5-bis(trifluoromethyl)phenyl]-2-((tert-butoxycarbonyl){[4'-fluoro-5'-isopropyl-2'-methoxy-4-(trifluoromethyl)biphenyl-2-yl]methyl}amino)propyl-4-{[tert-butoxycarbanyl)amino]methyl}-2-methoxyphenyl carbonate as a colorless oil. $R_f$=0.51 (20% EtOAc/hexanes). LCMS calc.=990.9; found=991.3 (M+H)⁺.

Step C: (1R,2S)-1-({[4-(Ammoniomethyl)-2-methoxyphenoxy]carbonyl}oxy)-1-[3,5-bis(trifluoromethyl)phenyl]-N-{[4'-fluoro-5'-isopropyl-2'-methoxy-4-(trifluoromethyl)biphenyl-2-yl]methyl}propan-2-aminium dichloride A solution of (1R,2S)-1-[3,5-bis(trifluoromethyl)phenyl]-2-((tert-butoxycarbonyl){[4'-fluoro-5'-isopropyl-2'-methoxy-4-(trifluoromethyl)biphenyl-2-yl]methyl}amino)propyl-4-{[tert-butoxycarbonyl)amino]methyl}-2-methoxyphenyl (50 mg, 0.050 mmol) in HCl saturated EtOAc (3 mL) was stirred at 25° C. for 3 h. The reaction mixture was concentrated in vacuo to afford (1R,2S)-1-({[4-(ammoniomethyl)-2-methoxyphenoxy]carbonyl}oxy)-1-[3,5-bis(trifluoromethyl)phenyl]-N-{[4'-fluoro-5'-isopropyl-2'-methoxy-4-

(trifluoromethyl)biphenyl-2-yl]methyl}propan-2-aminium dichloride as a white solid. LCMS calc.=790.7; found=791.1 (M+H)⁺.

Example 45

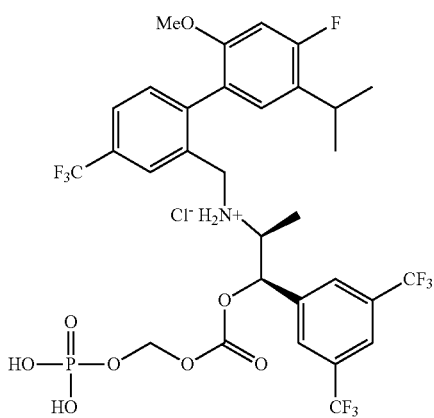

(7R,8S)-7-[3,5-Bis(trifluoromethyl)phenyl]-N-{[4'-fluoro-5'-isopropyl-2'-methoxy-4-(trifluoromethyl) biphenyl-2-yl]methyl}-1,1-dihydroxy-5-oxo-2,4,6-trioxa-1-phosphanonan-8-aminium-1-oxide chloride Step A: (1R,2S)-1-[3,5-Bis(trifluoromethyl)phenyl]-2-(tert-butoxycarbonyl){[4'-fluoro-5'-isopropyl-2'-methoxy-4-(trifluoromethyl)biphenyl-2-yl] methyl}amino)propyl chloromethyl carbonate Chloromethyl chloroformate (0.027 mL, 0.30 mmol) was added dropwise to a stirred solution of tert-butyl {(1S,2R)-2-[3,5-bis(trifluoromethyl)phenyl]-2-hydroxy-1-methylethyl}{[4'-fluoro-5'-isopropyl-2'-methoxy-4-(trifluoromethyl)biphenyl-2-yl]methyl}carbamate (INTERMEDIATE 7, 209 mg, 0.294 mmol) (200 mg, 0.28 mmol) and proton sponge (60 mg, 0.28 mmol) in dry CH₂Cl₂ (5.0 mL) at 0° C. under N₂. The reaction was stirred at 25° C. for 16 h. The reaction was diluted with water (30 mL) and extracted with EtOAc (3×30 mL). The combined extracts were dried (MgSO₄) and concentrated in vacuo to give the crude product. This was purified by flash chromatography (0-20% gradient EtOAc/hexanes over 30 min) to give (1R,2S)-1-[3,5-bis(trifluoromethyl)phenyl]-2-(tert-butoxycarbonyl){[4'-fluoro-5'-isopropyl-2'-methoxy-4-(trifluoromethyl)biphenyl-2-yl] methyl}amino)propyl chloromethyl carbonate as a colorless oil. ¹H NMR (500 MHz, CDCl₃): δ 7.81-6.82 (m, 8 H); 7.08 (dd, J=8.3 Hz, 8.7 Hz, 1 H); 5.68 (m, 2 H); 4.19-4.16 (d, J=16.7 Hz, 1 H); 4.77 (s, 3 H), 3.31-3.24 (m, 1 H); 1.76 (s, 3 H); 1.41 (s, 3 H); 1.22-1.18 (s, 9 H), 1.04 (d, J=6.6 Hz, 3 H).

Step B: {[Bis(benzyloxy)phosphoryl]oxy}methyl (1R,2S)-1-[3,5-bis(trifluoromethyl)phenyl]-2-(tert-butoxycarbonyl){[4'-fluoro-5'-isopropyl-2'-methoxy-4-(trifluoromethyl)biphenyl-2-yl]methyl}amino) propyl carbonate Silver dibenzylphosphate (22 mg, 0.056 mmol) was added to a solution of (1R,2S)-1-[3,5-bis(trifluoromethyl)phenyl]-2-(tert-butoxycarbonyl) {[4'-fluoro-5'-isopropyl-2'-methoxy-4-(trifluoromethyl)biphenyl-2-yl]methyl}amino)propyl chloromethyl carbonate (45 mg, 0.056 mmol) in dry toluene (3 mL) and the mixture was heated at reflux for 16 h. The precipitate formed was removed by filtration through a plug of Celite and washed with toluene (3×15 mL). The filtrate was concentrated in vacuo to give the crude product. This was purified by flash chromatography (0-20% EtOAc/hexanes) to afford {[bis(benzyloxy)phosphoryl]oxy}methyl(1R,2S)-1-[3,5-bis(trifluoromethyl)phenyl]-2-(tert-butoxycarbonyl){[4'-fluoro-5'-isopropyl-2'-methoxy-4-(trifluoromethyl)biphenyl-2-yl]methyl}amino)propyl carbonate, as a colorless oil. LCMS calc.=1045.89; found=1068.2 (M+Na)⁺.

Step C: (1R,2S)-1-[3,5-Bis(trifluoromethyl)phenyl]-2-(tert-butoxycarbonyl){[4'-fluoro-5'-isopropyl-2'-methoxy-4-(trifluoromethyl)biphenyl-2-yl] methyl}amino)propyl (phosphonooxy)methyl carbonate A suspension of 10% palladium on carbon (4.0 mg) and {[(bis(benzyloxy)phosphoryl]oxy}methyl(1R,2S)-1-[3,5-bis(trifluoromethyl)phenyl]-2-(tert-butoxycarbonyl){[4'-fluoro-5-isopropyl-2'-methoxy-4-(trifluoromethyl)biphenyl-2-yl]methyl}amino)propyl carbonate (17 mg, 0.016 mmol) in ethyl acetate (2.0 mL) was stirred under H₂ (double balloon pressure) at 25° C. for 16 h. The reaction mixture was filtered through a plug of Celite and the filtrate was concentrated in vacuo to afford (1R,2S)-1-[3,5-bis(trifluoromethyl)phenyl]-2-(tert-butoxycarbonyl){[4'-fluoro-5'-isopropyl-2'-methoxy-4-(trifluoromethyl)biphenyl-2-yl]methyl}amino)propyl (phosphonooxy)methyl carbonate. LCMS calc.=865.2; found=887.9 (M+Na)⁺.

Step D: (7R,8S)-7-[3,5-Bis(trifluoromethyl)phenyl]-N-{[4'-fluoro-5'-isopropyl-2'-methoxy-4-(trifluoromethyl)biphenyl-2-yl]methyl}-1,1-dihydroxy-5-oxo-2,4,6-trioxa-1-phosphanonan-8-aminium-1-oxide chloride A solution of (1R,2S)-1-[3,5-bis(trifluoromethyl)phenyl]-2-(tert-butoxycarbonyl){[4'-fluoro-5'-isopropyl-2'-methoxy-4-(trifluoromethyl)biphenyl-2-yl]methyl}amino)propyl (phosphonooxy)methyl carbonate (9 mg, 0.010 mmol) in HCl saturated EtOAc (3 mL) was stirred at 25° C. for 3 h. The reaction mixture was concentrated in vacuo to afford (7R,8S)-7-[3,5-bis(trifluoromethyl)phenyl]-N-{[4'-fluoro-5'-isopropyl-2'-methoxy-4-(trifluoromethyl)biphenyl-2-yl]methyl}-1,1-dihydroxy-5-oxo-2,4,6-trioxa-1-phosphanonan-8-aminium-1-oxide chloride, as a colorless oil/glass. LCMS calc.=801.2; found=803.4 (M+H)⁺.

Example 46

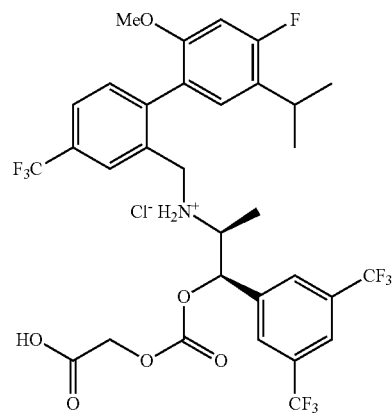

(1R,2S)-1-[3,5-Bis(trifluoromethyl)phenyl]-1-{[(carboxymethoxy)carbonyl]oxy}-N-{[4'-fluoro-5'-isopropyl-2'-methoxy-4-(trifluoromethyl)biphenyl-2-yl]methyl}propan-2-aminium chloride.

Step A: Benzyl (6R,7S)-6-[3,5-bis(trifluoromethyl)phenyl]-8-{[4'-fluoro-5'-isopropyl-2'-methoxy-4-(trifluoromethyl biphenyl-2-yl]methyl}-7,11,11-trimethyl-4,9-dioxo-3,5,10-trioxa-8-azadodecan-1-oate Pyridine (0.037 mL, 0.46 mmol) was added dropwise to a stirred solution of benzyl glycolate (76 mg, 0.46 mmol) and triphosgene (42 mg, 0.14 mmol) in dry $CH_2Cl_2$ (4.0 mL) at 0° C. under $N_2$. The reaction was stirred at 25° C. for 1.5 h. A solution of tert-butyl {(1S,2R)-2-[3,5-bis(trifluoromethyl)phenyl]-2-hydroxy-1-methylethyl}{[4'-fluoro-5'-isopropyl-2'-methoxy-4-(trifluoromethyl)biphenyl-2-yl]methyl}carbamate (INTERMEDIATE 7, 100 mg, 0.294 mmol) in dry $CH_2Cl_2$ (2 mL) was added followed by dropwise addition of pyridine (0.017 mL, 0.21 mmol). The reaction was stirred at 25° C. for 1 h. The reaction was diluted with water (15 mL) and extracted with EtOAc (3×20 mL). The combined extracts were dried ($MgSO_4$) and concentrated in vacuo to give the crude product. This was purified by flash chromatography (0-20% gradient EtOAc/hexanes over 30 min) to give benzyl(6R,7S)-6-[3,5-bis(trifluoromethyl)phenyl]-8-{[4'-fluoro-5'-isopropyl-2'-methoxy-4-(trifluoromethyl-biphenyl-2-yl]methyl}-7,11,11-trimethyl-4,9-dioxo-3,5,10-trioxa-8-azadodecan-1-oate as a colorless oil. $R_f$=0.51 (20% EtOAc/hexanes). LCMS calc.=903.8; found=926.0 $(M+Na)^+$.

Step B: (6R,7S)-6-[3,5-Bis(trifluoromethyl)phenyl]-8-{[4'-fluoro-5' sopropyl-2'-methoxy-4-(trifluoromethyl)biphenyl-2-yl]methyl}-7,11,11-trimehtyl-4,9-dioxo-3,5,10-trioxa-8-azadodecan-1-oic acid A suspension of 10% palladium on carbon (3.0 mg), benzyl (6R,7S)-6-[3,5-bis(trifluoromethyl)phenyl]-8-{[4'-fluoro-5'-isopropyl-2'-methoxy-4-(trifluoromethyl-biphenyl-2-yl]methyl}-7,11,11-trimethyl-4,9-dioxo-3,5,10-trioxa-8-azadodecan-1-oate (25 mg, 0.028 mmol) and 1-methyl 1,4-cyclohexadiene (26 mg, 0.28 mmol) in ethanol (2.0 mL) was stirred at 25° C. for 16 h. The reaction mixture was filtered through a plug of Celite and the filtrate was concentrated in vacuo to (6R,7S)-6-[3,5-bis(trifluoromethyl)phenyl]-8-{[4'-fluoro-5'-isopropyl-2'-methoxy-4-(trifluoromethyl)biphenyl-2-yl]methyl}-7,11,11-trimehtyl-4,9-dioxo-3,5,10-trioxa-8-azadodecan-1-oic acid. LCMS calc.=813.7; found=835.9 $(M+Na)^+$.

Step C: (1R,2S)-1-[3,5-Bis(trifluoromethyl)phenyl]-1-{[(carboxymethoxy)carbonyl]oxy}-N-{[4'-fluoro-5'-isopropyl-2'-methoxy-4-(trifluoromethyl)biphenyl-2-yl]methyl}propan-2-aminium chloride A solution of (6R,7S)-6-[3,5-bis(trifluoromethyl)phenyl]-8-{[4'-fluoro-5'-isopropyl-2'-methoxy-4-(trifluoromethyl)biphenyl-2-yl]methyl}-7,11,11-trimethyl-4,9-diaxo-3,5,10-trioxa-8-azadodecan-1-oic acid (6 mg, 0.007 mmol) in HCl saturated EtOAc (2 mL) was stirred at 25° C. for 3 h. The reaction mixture was concentrated in vacuo to afford (1R,2S)-1-[3,5-bis(trifluoromethyl)phenyl]-1-{[(carboxymethoxy)carbonyl]oxy}-N-{[4'-fluoro-5'-isopropyl-2'-methoxy-4-(trifluoromethyl)biphenyl-2-yl]methyl}propan-2-aminium chloride, as a colorless oil/glass. LCMS calc.=713.6; found=713.9 $(M+H)^+$.

Example 47

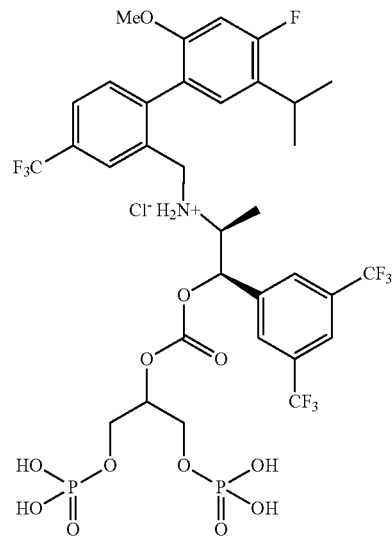

(8R,9S)-8-[3,5-bis(trifluoromethyl)phenyl]-N-{[4'-fluoro-5'-isopropyl-2'-methoxy-4-(trifluoromethyl)biphenyl-2-yl]methyl}-1,1-dihydroxy-6-oxo-4-[(phosphonooxy)methyl]-2,5,7-trioxa-1$\lambda^5$-phosphadecan-9-aminium1-oxide chloride Step A: (1R,2S)-1-[3,5-Bis(trifluoromethyl)phenyl]-2-((tert-butoxycarbonyl){[4'-fluoro-5'-isopropyl-2'-methoxy-4-(trifluoromethyl)biphenyl-2-yl]methyl}amino)propyl 2-phenyl-1,3-dioxan-5-yl carbonate Pyridine (0.035 mL, 0.437 mmol) was added dropwise to a stirred solution of 1,3-benzylidene glycerol (79 mg, 0.437 mmol) and triphosgene (47.4 mg, 0.160 mmol) in dry $CH_2Cl_2$ (4.00 mL) at 0° C. under $N_2$. The reaction was stirred at 25° C. for 1.5 h. A solution of tert-butyl {(1S,2R)-2-[3,5-bis(trifluoromethyl)phenyl]-2-hydroxy-1-methylethyl)}{[4'-fluoro-5'-isopropyl-2'-methoxy-4-(trifluoromethypbiphenyl-2-yl]methyl}carbamate (155.6 mg, 0.219 mmol) in dry $CH_2Cl_2$ (2.00 mL) was added via cannula followed by dropwise addition of pyridine (0.040 mL, 0.492 mmol) The reaction was stirred overnight at 25° C. The reaction was diluted with water (15 mL) and extracted with EtOAc (3×20 mL). The combined extracts were dried ($MgSO_4$) and concentrated in vacuo to give the crude product. This was purified by flash chromatography (Biotage Horizon, 25M, Si, ~20 mL/min, 100% hexanes for 144 mL, gradient to 20% EtOAc in hexanes over 2394 mL) to afford (1R,2S)-1-[3,5-bis(trifluoromethyl)phenyl]-2-((tert-butoxycarbonyl){[4'-fluoro-5'-isopropyl-2'-methoxy-4-(trifluoromethyl)biphenyl-2-yl]methyl}amino)propyl 2-phenyl-1,3-dioxan-5-yl carbonate, as a colorless oil. $R_f$=0.46 (20% EtOAc in hexanes). LCMS calc.=940.29; found=940.10 $(M+Na)^+$.

Step B: (1R,2S)-1-[3,5-Bis(trifluoromethyl)phenyl]-
2-((tert-butoxycarbonyl){[4'-fluoro-5'-isopropyl-2'-
methoxy-4-(trifluoromethyl)biphenyl-2-yl]
methyl}amino)propyl 2-hydroxy-1-(hydroxymethyl)
ethyl carbonate A suspension of 10% palladium on carbon (9.13 mg, 8.57 µmol) in a solution of (1R,2S)-1-[3,5-bis(trifluoromethyl) phenyl]-2-((tert-butoxycarbonyl){[4'-fluoro-5'-isopropyl-2'-methoxy-4-(trifluoromethyl)biphenyl-2-yl]methyl}amino) propyl 2-phenyl-1,3-dioxan-5-yl carbonate (78.7 mg, 0.086 mmol) in EtOAc (6.60 mL) was stirred under $H_2$ (double balloon pressure) at 25° C. for 15 h. The reaction mixture was filtered through a plug of Celite and the filtrate was concentrated in vacuo to afford (1R,2S)-1-[3,5-bis(trifluoromethyl) phenyl]-2-((tert-butoxycarbonyl){[4'-fluoro-5'-isopropyl-2'-methoxy-4-(trifluoromethyl)biphenyl-2-yl]methyl}amino) propyl 2-hydroxy-1-(hydroxymethyl)ethyl carbonate. LCMS calc.=852.26; found=852.10 (M+Na)$^+$.

Step C: 2-{[Bis(benzyloxy)phosphoryl]oxy}-1-({[bis
(benzyloxy)phosphoryl]oxy}methyl)ethyl (1R,2S)-1-
[3,5-bis(trifluoromethyl)phenyl]-2-((tert-butoxycar-
bonyl){[4'-fluoro-5'-isopropyl-2'-methoxy-4-
(trifluoromethyl)biphenyl-2-yl]methyl}amino)propyl
carbonate Dibenzyl N,N-diisopropylphosphoramidite (78 µL, 0.231 mmol) was added to a stirred solution of 1H-tetrazole (0.45 M in $CH_3CN$) (1027 µl, 0.462 mmol) and (1R,2S)-1-[3,5-bis (trifluoromethyl)phenyl]-2-((tert-butoxycarbonyl){[4'-fluoro-5'-isopropyl-2'-methoxy-4-(trifluoromethyl)biphenyl-2-yl]methyl}amino)propyl 2-hydroxy-1-(hydroxymethyl)ethyl carbonate (63.9 mg, 0.077 mmol) in dry $CH_2Cl_2$ (2.85 mL) at 25° C. under $N_2$. The reaction was stirred for 3 h at 25° C. The reaction mixture was cooled to 0° C. and a solution of 3-chloroperoxybenzoic acid (69.0 µL, 0.308 mmol) in dry $CH_2Cl_2$ (1.43 mL) was added via cannula and the reaction was stirred at 0° C. After 60 min the reaction was diluted with EtOAc (25 mL) and washed with successive portions of saturated $Na_2SO_3$ (20 mL) and saturated $NaHCO_3$ (20 mL), dried ($Na_2SO_4$) and concentrated in vacuo to afford the crude product. This was purified by flash chromatography (Biotage Horizon, 25M, Si, ~20 mL/min, 100% hexanes for 144 mL, gradient to 50% EtOAc in hexanes over 2394 mL, gradient to 100% EtOAc over 1269 mL) to afford 2-{[bis (benzyloxy)phosphoryl]oxy}-1-({[bis(benzyloxy)phospho-ryl]oxy}methyl)ethyl (1R,2S)-1-[3,5-bis(trifluoromethyl) phenyl]-2-((tert-butoxycarbonyl){[4'-fluoro-5'-isopropyl-2'-methoxy-4-(trifluoromethyl)biphenyl-2-yl]methyl}amino) propyl carbonate, as a colorless oil. $R_f$=0.61 (50% EtOAc in hexanes). LCMS calc.=1350.40; found=1350.47 (M+H)$^+$.

Step D: (1R,2S)-1-[3,5-Bis(trifluoromethyl)phenyl]-
2-((tert-butoxycarbonyl){[4'-fluoro-5'-isopropyl-2'-
methoxy-4-(trifluoromethyl)biphenyl-2-yl]
methyl}amino)propyl 2-(phosphonooxy)-1-
[(phosphonooxy)methyl]ethyl carbonate A suspension of 10% palladium on carbon (6.0 mg, 5.65 µmol) in a solution of 2-{[bis(benzyloxy)phosphoryl]oxy}-1-({[bis(benzyloxy)phosphoryl]oxy}methyl)ethyl (1R,2S)-1-[3,5-bis(trifluoromethyl)phenyl]-2-((tert-butoxycarbonyl) {[4'-fluoro-5'-isopropyl-2'-methoxy-4-(trifluoromethyl) biphenyl-2-yl]methyl}amino)propyl carbonate in ethanol (4.35 mL) was stirred under $H_2$ (double balloon pressure) at 25° C. for 3 h. The reaction mixture was filtered through a Teflon filter and the filtrate was concentrated in vacuo to afford (1R,2S)-1-[3,5-bis(trifluoromethyl)phenyl]-2-((tert-butoxycarbonyl){[4'-fluoro-5'-isopropyl-2'-methoxy-4-(trifluoromethyl)biphenyl-2-yl]methyl}amino)propyl 2-(phosphonooxy)-1-[(phosphonooxy)methyl]ethyl carbonate. LCMS calc.=1012.19; found=1012.20 (M+Na)$^+$.

Step E: (8R,9S)-8-[3,5-Bis(trifluoromethyl)phenyl]-
N-{[4'-fluoro-5'-isopropyl-2'-methoxy-4-(trifluorom-
ethyl)biphenyl-2-yl]methyl}-1,1-dihydroxy-6-oxo-4-
[(phosphonooxy)methyl]-2,5,7-trioxa-1λ5-
phosphadecan-9-aminium 1-oxide chloride A solution of (1R,2S)-1-[3,5-bis(trifluoromethyl)phenyl]-2-((tert-butoxycarbonyl){[4'-fluoro-5'- isopropyl-2'-methoxy-4-(trifluoromethyl)biphenyl-2-yl]methyl}amino)propyl 2-(phosphonooxy)-1-[(phosphonooxy)methyl]ethyl carbonate (46.7 mg, 0.047 mmol) in HCl saturated EtOAc (3 mL) was stirred at 25° C. for 1 h. The reaction mixture was concentrated in vacuo to afford (8R,9S)-8-[3,5-bis(trifluoromethyl)phenyl]-N-{[4'-fluoro-5'-isopropyl-2'-methoxy-4-(trifluoromethyl)biphenyl-2-yl]methyl}-1,1-dihydroxy-6-oxo-4-[(phosphonooxy)methyl]-2,5,7-trioxa-1λ5-phosphadecan-9-aminium 1-oxide chloride, as a colorless glass/solid. LCMS calc.=890.16; found=890.00 (M+H)$^+$.

Example 48

Cyclization Reactions

The kinetics of the cyclization reactions of the compounds described herein could be followed by the procedure illustrated below for the compound of EXAMPLE 35.

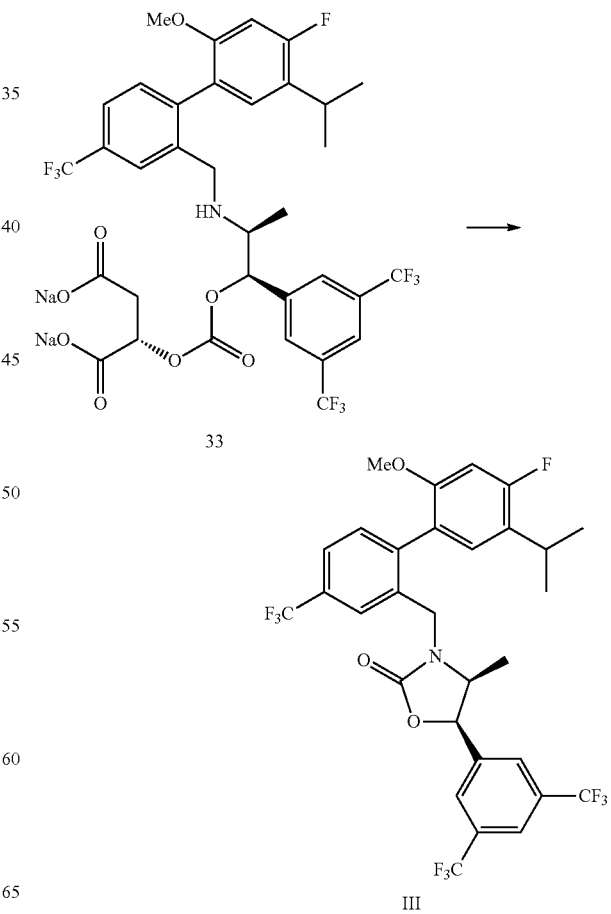

The sodium salt of EXAMPLE 35 (20 mg, 0.025 mmol) was dissolved (sonicated to ensure dissolution) in 100 mM sodium phosphate buffer in D$_2$O (pH 7.52, 2.2 mL) and heated at 37° C. in an oil bath. 50 μL aliquots were removed periodically. An aliquot was taken at 3 minutes, then every 15 minutes until 135 minutes from the start, then every 30 minutes until 225 minutes from the start. Each aliquot was diluted with MeCN-d$_3$ (150 μL), and a $^1$H NMR spectrum was acquired (128 scans at 25° C., with acquisition starting 3 minutes after the aliquot was taken from the reaction). The t$_{1/2}$ was determined by examining the spectra to find the point in time where the ratio of starting material (SM) and product was 1:1, based on 2 independent resolved signals in the aromatic region. The t$_{1/2}$ was found to be 75-90 min. Liquid chromatography-mass spectrometry (LCMS) of the reaction mixture showed the oxazolidinone III to be the main product. A small amount of SM remained along with a compound having a minor NMR peak that may be attributed to the corresponding carbamate. A small amount (ca. 1%) of the monoethyl ester byproduct was also present as a contaminant from the BOC deprotection step.

Table 4 below provides half-life data for some of the compounds described above. The methods for determining the half-lives were approximately the same as described above, with variations in procedure depending on such variables as solubility and reaction rates. The cyclizations using the compounds of EXAMPLES 37, 38, and 47 were carried out in a mixed solvent (D$_2$O/1,4-dioxane-d$_8$=1:3) rather than a single solvent (D$_2$O).

TABLE 4

| Example No | Half Life of Cyclization at 37° C. | pH of solution |
| --- | --- | --- |
| 35 | 75-90 minutes | 7.52 |
| 36 | 135-150 minutes | 7.52 |
| 37 | ~4 hours | 7.68 |
| 47 | ~150 minutes | 7.68 |
| 38 | 9-10 hours | 7.68 |

It can be seen from the half-life data that different structures have different half lives for cyclization. The half-life can thus be adjusted by a practitioner in the art by making structural changes in the Z group, thereby optimizing the rate of cyclization to maximize the amount of absorption and minimize the magnitude of the food effect.

What is claimed is:

1. A compound of formula I, or a pharmaceutically acceptable salt thereof:

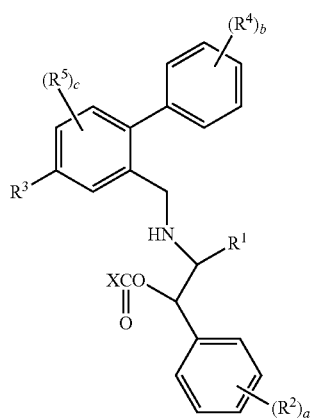

I wherein R$^1$ is selected from H and C$_{1-4}$alkyl, which is optionally substituted with 1-5 F groups;

Each R$^2$ is independently selected from the group consisting of halogen, —CN, C$_{1-4}$alkyl, and —OC$_{1-4}$alkyl, wherein C$_{1-4}$alkyl and —OC$_{1-4}$alkyl are optionally substituted with 1-5 halogens;

R$^3$ is selected from the group consisting of H, halogen, C$_{1-4}$alkyl, and —OC$_{1-4}$alkyl, wherein C$_{1-4}$alkyl and —OC$_{1-4}$alkyl are optionally substituted with 1-5 halogens;

R$^4$ and R$^5$ are each independently selected from the group consisting of halogen, C$_{1-4}$alkyl, and —OC$_{1-4}$alkyl, wherein C$_{1-4}$alkyl and —OC$_{1-4}$alkyl are optionally substituted with 1-5 halogens;

R$^6$ is selected from H and C$_1$-C$_5$ alkyl optionally substituted with 1-5 halogens and optionally substituted with 1-2 phenyl groups, wherein phenyl is optionally substituted with 1-3 groups independently selected from halogen, C$_1$-C$_3$ alkyl, —OC$_1$-C$_3$ alkyl, CF$_3$, and —OCF$_3$;

R$^7$ is selected from H and C$_1$-C$_3$ alkyl optionally substituted with 1-3 F;

X is selected from —OZ and —SZ, wherein Z is selected from:

(a) C$_1$-C$_5$ alkyl which optionally includes an —O— atom between 2 adjacent carbon atoms, wherein C$_1$-C$_5$ alkyl is optionally substituted with 1-5 halogens and is optionally substituted with 1-2 substituent groups independently selected from phenyl, —C(=O)OR$^6$, —OP(=O)(OR$^7$)$_2$, and —P(=O)(OR$^7$)$_2$, wherein phenyl is optionally substituted with 1-3 groups independently selected from halogen, —C(=O)OR$^7$, and C$_1$-C$_3$alkyl optionally substituted with 1-3 halogens; and (b) phenyl, wherein phenyl is optionally substituted with 1-3 groups independently selected from halogen; C$_1$-C$_5$alkyl; —OC$_1$-C$_5$alkyl; —C(=O)OR$^7$; and C$_5$-C$_7$cycloalkyl optionally substituted with 1-2 groups independently selected from halogen, C$_1$-C$_3$alkyl, —OC$_1$-C$_3$alkyl, CF$_3$, and —OCF$_3$; wherein C$_1$-C$_5$alkyl and —OC$_1$-C$_5$alkyl are optionally substituted with 1-5 F and are optionally substituted with 1-2 groups independently selected from —C(=O)OR$^7$, —N(R$^7$)$_2$, —OP(=O)(OR$^7$)$_2$, and —P(=O)(OR$^7$)$_2$;

a and b are integers independently selected from 0-4; and c is an integer from 0-2.

2. The compound of claim 1, wherein

Z is selected from (a) C$_1$-C$_5$ alkyl which optionally includes an —O— atom between 2 adjacent carbon atoms, wherein C$_1$-C$_5$ alkyl is optionally substituted with 1-3 F and is optionally substituted with 1-2 substituent groups independently selected from phenyl, —C(=O)OR$^6$, —OP(=O)(OR$^7$)$_2$, and —P(=O)(OR$^7$)$_2$, wherein phenyl is optionally substituted with 1-3 groups independently selected from halogen, C$_1$-C$_3$alkyl, CF$_3$, and —C(=O)OR$^7$; and (b) Phenyl, wherein phenyl is optionally substituted with 1-3 groups independently selected from halogen; C$_1$-C$_5$alkyl; CF$_3$; —OC$_1$-C$_3$alkyl; —OCF$_3$; —C(=O)OR$^7$; and C$_5$-C$_6$cycloalkyl which is optionally substituted with 1-2 groups independently selected from halogen, CH$_3$, and —OCH$_3$; wherein C$_1$-C$_5$alkyl and —OC$_1$-C$_3$alkyl are optionally substituted with 1-2 groups independently selected from —C(=O)OR$^7$, —N(R$^7$)$_2$, —OP(=O)(OR$^7$)$_2$; and —P(=O)(OR$^7$)$_2$.

3. The compound of claim 2, wherein $R^1$ is $C_{1-2}$ alkyl, optionally substituted with 1-3 F;

Each $R^2$ is independently selected from —CN, $C_{1-3}$alkyl, $CF_3$, —$OCH_3$, —$OCF_3$, and F;

$R^3$ is selected from $C_{1-3}$alkyl, —$OC_{1-3}$alkyl, and F, wherein $C_{1-3}$alkyl and $OC_{1-3}$alkyl are optionally substituted with 1-5 F;

$R^4$ and $R^5$ are each independently selected from $C_{1-3}$alkyl, $CF_3$, —$OCH_3$, —$OCF_3$, and F;

$R^6$ is selected from H and $C_1$-$C_2$alkyl, wherein $C_1$-$C_2$alkyl is optionally substituted with one phenyl group, said phenyl being optionally substituted with 1-3 groups independently selected from halogen, $CH_3$, $CF_3$, —$OCH_3$, and —$OCF_3$;

$R^7$ is selected from H and $C_1$-$C_3$ alkyl optionally substituted with 1-3 F;

a is 1 or 2;

b is an integer from 1-3; and c is 0 or 1.

4. The compound of claim 3, wherein

X is selected from —$SC_1$-$C_2$alkyl and —OZ;

Z is selected from the group consisting of (a) —($CH_2CH_2O$—)$_n$$C_1$-$C_3$alkyl, wherein $C_1$-$C_3$alkyl is optionally substituted with 1-2 substituent groups independently selected from phenyl, —C(=O)$OR^6$, —OP(=O)($OR^7$)$_2$, and —P(=O)($OR^7$)$_2$, wherein phenyl is optionally substituted with one group —C(=O)$OR^7$; and (b) phenyl, which is optionally substituted with 1-3 substituents independently selected from $C_1$-$C_4$ alkyl, —$OC_1$-$C_3$alkyl, —C(=O)$OR^7$, and cyclohexyl, wherein $C_1$-$C_4$ alkyl and —$OC_1$-$C_3$alkyl are optionally substituted with 1-2 groups independently selected from —N($R^7$)$_2$, —C(=O)$OR^7$, and —OP(=O)($OR^7$)$_2$; and n is an integer selected from 0 and 1.

5. The compound of claim 4, wherein $R^1$ is $C_{1-2}$ alkyl;

$R^2$ is $CF_3$;

$R^3$ is selected from $CH_3$, $CF_3$ and F;

Each $R^4$ is independently selected from $C_{1-3}$alkyl, —$OCH_3$, and F;

$R^6$ is selected from H, $C_1$-$C_2$alkyl, and —$CH_2$phenyl;

$R^7$ is selected from H and $C_1$-$C_2$alkyl;

a is 2;

b is 2 or 3; and c is 0.

6. The compound of claim 5, wherein $R^1$ is $CH_3$; and b is 3.

7. The compound of claim 1 having formula IV, or a pharmaceutically acceptable salt thereof:

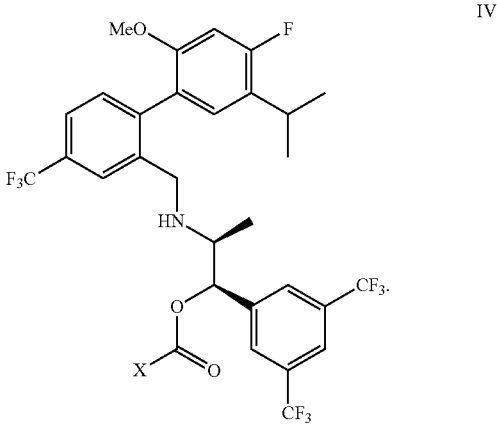

IV

8. The compound of claim 7, wherein Z is selected from the group consisting of:

(a) $C_1$-$C_5$ alkyl which optionally includes an —O— atom between 2 adjacent carbon atoms, wherein $C_1$-$C_5$ alkyl is optionally substituted with 1-3 F and is optionally substituted with 1-2 substituent groups independently selected from phenyl, —C(=O)$OR^6$, —OP(=O)($OR^7$)$_2$, and —P(=O)($OR^7$)$_2$, wherein phenyl is optionally substituted with 1-3 groups independently selected from halogen, $C_1$-$C_3$alkyl, $CF_3$, and —C(=O)$OR^7$; and (b) Phenyl, wherein phenyl is optionally substituted with 1-3 groups independently selected from halogen; $C_1$-$C_5$alkyl; $CF_3$; —$OC_1$-$C_3$alkyl; —$OCF_3$; —C(=O)$OR^7$, and $C_5$-$C_6$cycloalkyl which is optionally substituted with 1-2 groups independently selected from halogen, $CH_3$, and —$OCH_3$; wherein $C_1$-$C_5$alkyl and —$OC_1$-$C_3$alkyl are optionally substituted with 1-2 groups independently selected from —C(=O)$OR^7$, —N($R^7$)$_2$, —OP(=O)($OR^7$)$_2$, and —P(=O)($OR^7$)$_2$.

9. The compound of claim 8, wherein

X is selected from —$SC_1$-$C_2$alkyl and —OZ;

Z is selected from the group consisting of (a) —($CH_2CH_2O$—)$_n$$C_1$-$C_3$ alkyl, wherein $C_1$-$C_3$ alkyl is optionally substituted with 1-2 substituent groups independently selected from phenyl, —C(=O)$OR^6$, —OP(=O)($OR^7$)$_2$, and —P(=O)($OR^7$)$_2$, wherein phenyl is optionally substituted with one group —C(=O)$OR^7$; and (b) phenyl, which is optionally substituted with 1-3 substituents independently selected from $C_1$-$C_4$ alkyl, —$OC_1$-$C_3$alkyl, —C(=O)$OR^7$, and cyclohexyl, wherein $C_1$-$C_4$alkyl and —$OC_1$-$C_3$alkyl are optionally substituted with 1-2 groups independently selected from —N($R^7$)$_2$, —C(=O)$OR^7$, and —OP(=O)($OR^7$)$_2$;

n is an integer selected from 0 and 1; and $R^6$ is selected from the group consisting of H and $C_1$-$C_2$alkyl which is optionally substituted with one phenyl group, said phenyl being optionally substituted with 1-3 groups independently selected from halogen, $CH_3$, $CF_3$, —$OCH_3$, and —$OCF_3$.

10. The compound of claim 9, wherein

X is selected from —$SC_1$-$C_2$alkyl and —OZ;

Z is selected from the group consisting of:

(a) —($CH_2CH_2O$—)$_n$$C_1$-$C_3$ alkyl, wherein $C_1$-$C_3$alkyl is optionally substituted with 1-2 substituent groups independently selected from phenyl, —C(=O)OR⁶, —OP(=O)(OR⁷)₂, and —P(=O)(OR⁷)₂, wherein phenyl is optionally substituted with one group —C(=O)OR⁷; and (b) phenyl, which is substituted with 1-3 substituents independently selected from $C_1$-$C_4$ alkyl, —O$C_1$-$C_3$alkyl, —C(=O)OR⁷, and cyclohexyl, wherein $C_1$-$C_4$alkyl and —O$C_1$-$C_3$alkyl are optionally substituted with 1-2 groups independently selected from —N(R⁷)₂, —C(=O)OR⁷, and —OP(=O)(OR⁷)₂;

R⁶ is selected from H, $C_1$-$C_2$alkyl, and —CH₂phenyl; and

R⁷ is selected from H and $C_1$-$C_2$alkyl.

11. The compound of claim 10, wherein X is —OZ.

12. A pharmaceutical composition comprising the compound of claim 1, or a pharmaceutically acceptable salt thereof, and a pharmaceutically acceptable carrier.

13. The compound of claim 10, or a pharmaceutically acceptable salt thereof, wherein the compound has a structure which is selected from the group consisting of the following structures:

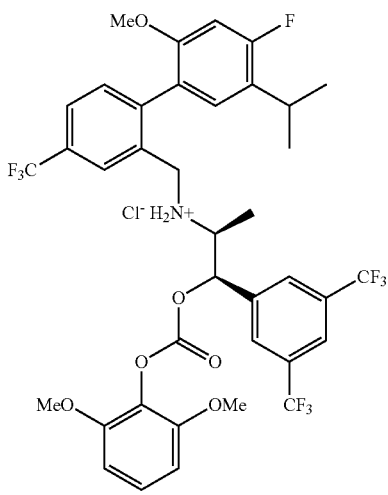

Ex. 1

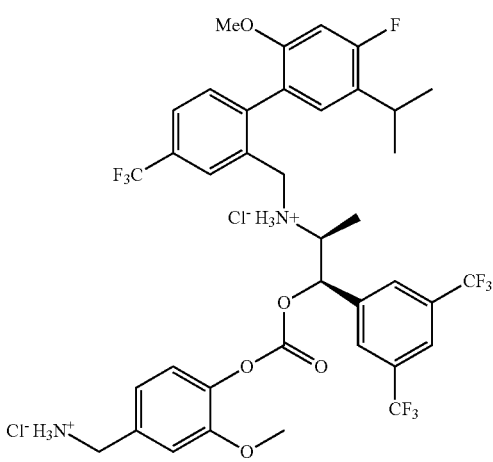

Ex. 44

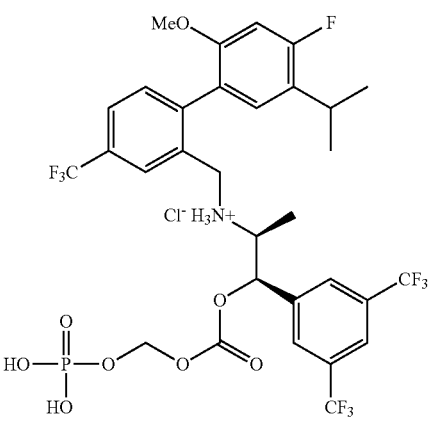

Ex. 45

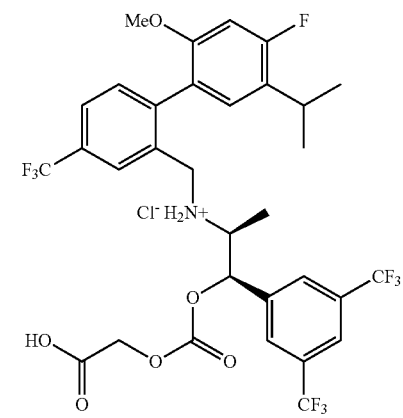

Ex. 46

Ex. 32

Ex. 47
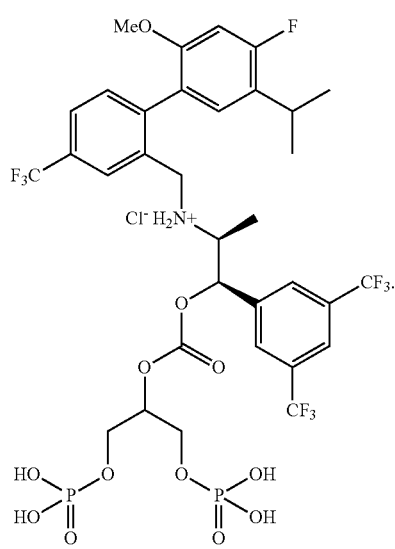
14. The compound of claim 10, or a pharmaceutically acceptable salt thereof, wherein the compound has a structure which is selected from the group consisting of the following structures:
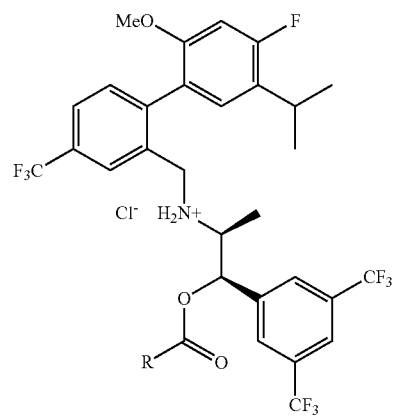
R
Ex. 2
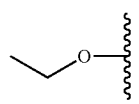 [SMILES: *OCC]
Ex. 3
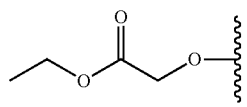 [SMILES: *OCC(=O)OCC]
Ex. 4
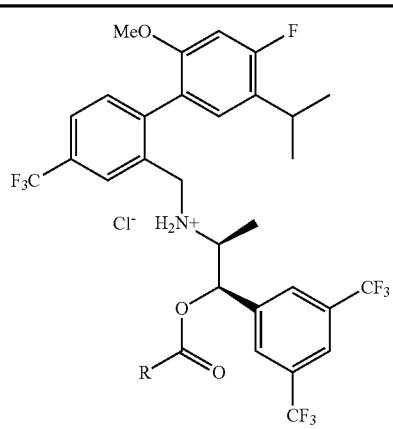
R
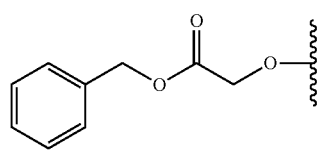 [SMILES: *OCC(=O)OCc1ccccc1]
Ex. 5
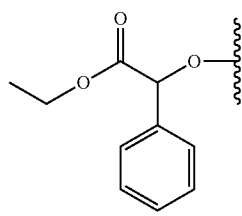 [SMILES: *OC(C(=O)OCC)c1ccccc1]
Ex. 6
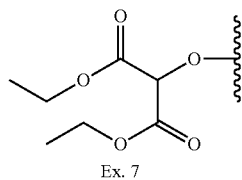
Ex. 7
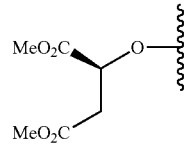 [SMILES: *O[C@@H](CC(=O)OC)C(=O)OC]
Ex. 8
Ex. 9
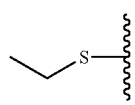
Ex. 10

| 49 -continued | 50 -continued |
|---|---|

Structure (both columns): biphenyl with MeO, F, isopropyl, CF₃ substituents; benzylic CH₂ linked to NH₂⁺·Cl⁻ bearing a methyl group; attached to CH–O–C(=O)–R with 3,5-bis(trifluoromethyl)phenyl group.

| R | R |
|---|---|
| Benzyl-O- (PhCH₂O-) — Ex. 11 | 2,3-dimethoxyphenoxy (MeO, OMe) — Ex. 17 |
| 4-(MeO₂C)-benzyl-O- — Ex. 12 | 2-(Oi-Pr)-phenoxy — Ex. 18 |
| 4-MeO-phenoxy — Ex. 13 | 4-MeO-2-(Oi-Pr)-phenoxy — Ex. 19 |
| 2,3,5-trimethoxyphenoxy (MeO, MeO, OMe) — Ex. 14 | 2-methylphenoxy — Ex. 20 |
| 2,4-dimethoxyphenoxy (MeO, OMe) — Ex. 15 | 2-isopropylphenoxy — Ex. 21 |
| 2,3,4-trimethoxyphenoxy (MeO, OMe, OMe) — Ex. 16 | 2-tert-butylphenoxy — Ex. 22 |

| 51 -continued | 52 -continued |
|---|---|
| 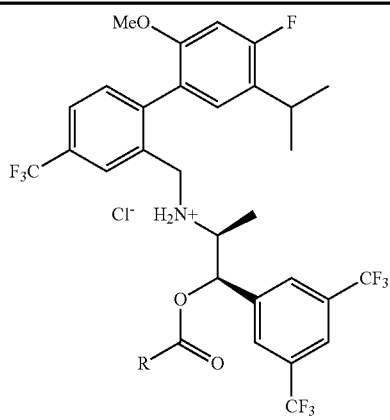 | 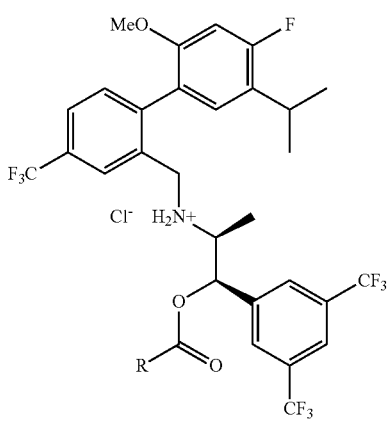 |
| R | R |
| 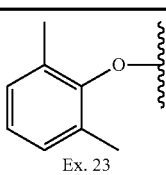<br>Ex. 23 | |
| 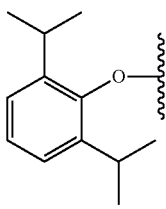 [SMILES: *Oc1c(C(C)C)cccc1C(C)C]<br>Ex. 24 | 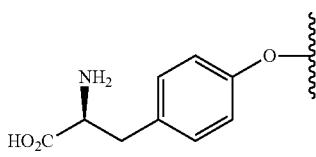<br>Ex. 29 |
| 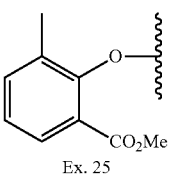<br>Ex. 25 | 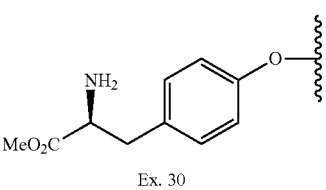<br>Ex. 30 |
| 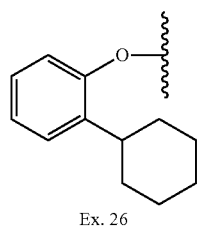<br>Ex. 26 | 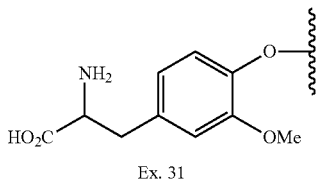<br>Ex. 31 |
| 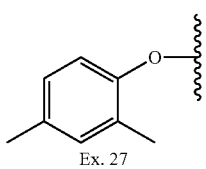<br>Ex. 27 | 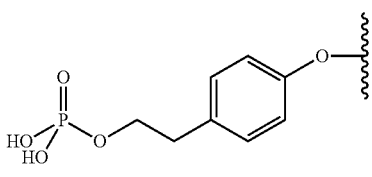<br>Ex. 33 |
| 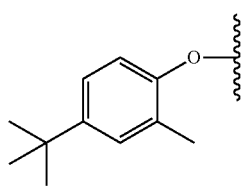 [SMILES: *Oc1ccc(C(C)(C)C)cc1C]<br>Ex. 28 | 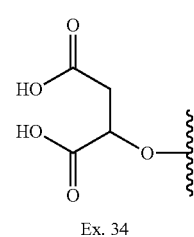<br>Ex. 34 |

| 53 -continued | 54 -continued |
|---|---|
| 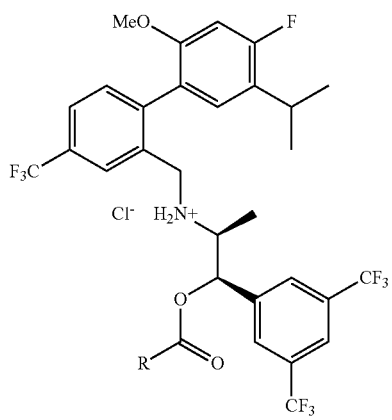 | 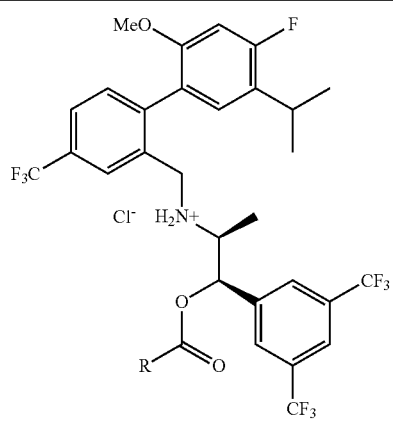 |
| R | R |
| 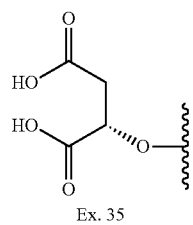
Ex. 35 | 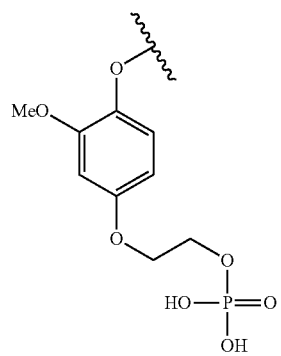
Ex. 39 |
| 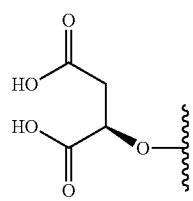 [SMILES: *O[C@H](CC(=O)O)C(=O)O]
Ex. 36 | |
| 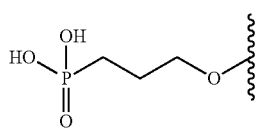 [SMILES: *OCCCP(=O)(O)O]
Ex. 37 | 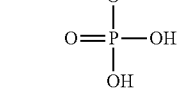 |
| 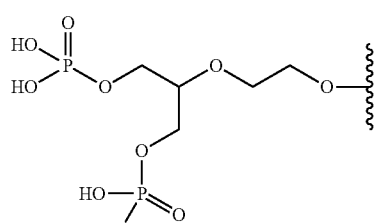
Ex. 38 | Ex. 40 |

-continued

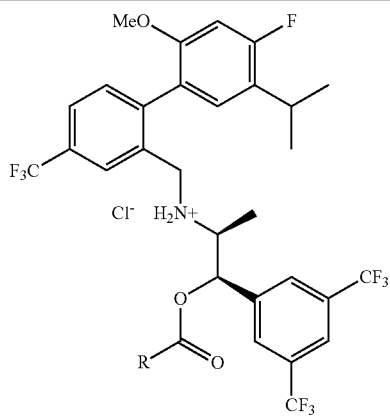

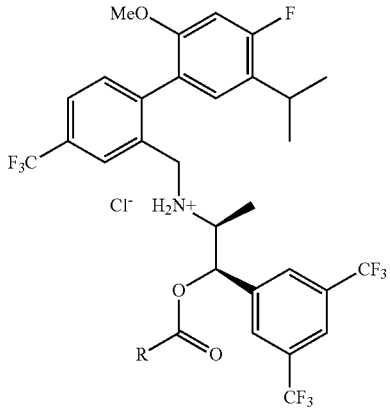

R

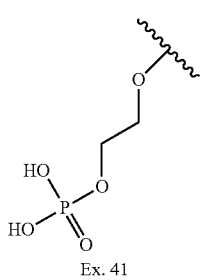

Ex. 41

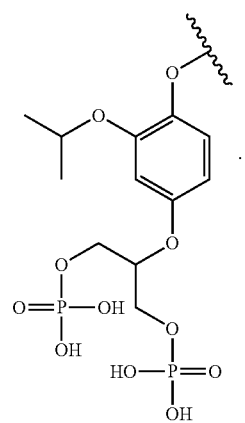 [SMILES: *Oc1ccc(OC(COP(=O)(O)O)COP(=O)(O)O)cc1OC(C)C]

Ex. 43

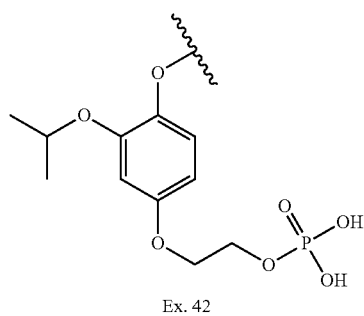

Ex. 42

15. A method of raising HDL-cholesterol in a patient in need of treatment, comprising the administration of the compound of claim 1, or a pharmaceutically acceptable salt thereof to the patient.

16. A method of lowering LDL-cholesterol in a patient in need of treatment, comprising the administration of the compound of claim 1, or a pharmaceutially acceptable salt thereof to the patient.

17. A method of treating hypercholesterolemia in a patient in need of treatment, comprising the administration of the compound of claim 1, or a pharmaceutically acceptable salt thereof to the patient.

* * * * *